US007615653B2

(12) United States Patent
Ojima

(10) Patent No.: US 7,615,653 B2
(45) Date of Patent: Nov. 10, 2009

(54) ANTI-TUBERCULOSIS TAXANE COMPOUNDS

(75) Inventor: Iwao Ojima, Port Jefferson, NY (US)

(73) Assignee: The Research Foundation of State University of New York, Albany, NY (US)

( * ) Notice: Subject to any disclaimer, the term of this patent is extended or adjusted under 35 U.S.C. 154(b) by 226 days.

(21) Appl. No.: 11/684,883

(22) Filed: Mar. 12, 2007

(65) Prior Publication Data

US 2008/0081836 A1    Apr. 3, 2008

Related U.S. Application Data

(60) Provisional application No. 60/782,346, filed on Mar. 15, 2006.

(51) Int. Cl.
C07D 305/00     (2006.01)
(52) U.S. Cl. .................................. 549/511
(58) Field of Classification Search ............ 549/511
See application file for complete search history.

(56) References Cited

U.S. PATENT DOCUMENTS 5,705,508 A    1/1998   Ojima et al. ............. 514/320

OTHER PUBLICATIONS

J. Med. Chem. 2006, 49, 463-466; Targeting FtsZ for Antituberculosis Drug Discovery: Noncytotoxic Taxanes as Novel Antituberculosis Agents; 2006, American Chemical Society, Published Dec. 21, 2005.
Tetrahedron Letters, vol. 38, No. 24, pp. 4273-4276, 1997, Elsevier Science Ltd.; Synthesis and Evaluation of C-Seco Paclitaxel Analogues, Geovanni Appendino, etl al.
1182 vol. 8, 1182-1188, Apr. 2002, Clinical Cancer Research, Antiangiogenic and Antitumor Activity of IDN 5390, a New Taxane Derivative.

*Primary Examiner*—Janet L. Andres
*Assistant Examiner*—Raymond Covington
(74) *Attorney, Agent, or Firm*—Hoffmann & Baron, LLP

(57) ABSTRACT

The present invention relates to compounds having the formula (I):

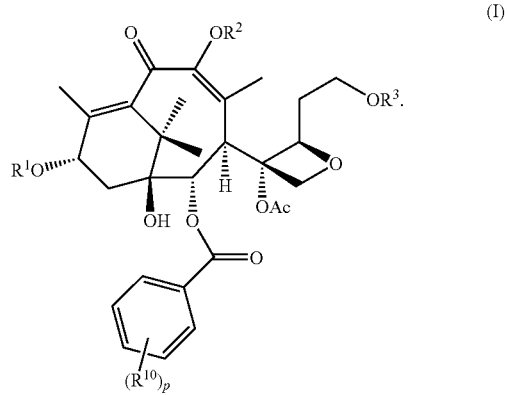

22 Claims, No Drawings

ANTI-TUBERCULOSIS TAXANE COMPOUNDS

This application claims the benefit of U.S. provisional application 60/782,346 filed Mar. 15, 2006.

BACKGROUND OF THE INVENTION

The present invention relates to taxane compounds possessing strong anti-tuberculosis activity, compositions including these compounds, processes for synthesizing these compounds, and methods for treating patients suffering from tuberculosis.

Tuberculosis is the leading cause of death in the world from a infectious disease. The cause of tuberculosis is the bacterium *Mycobacterium tuberculosis* (MTB), and most commonly infects the respiratory system. Tuberculosis patients have been traditionally been prescribed a course of drug treatment to eliminate MTB from the patient's body.

However, drug resistance of MTB has been become an increasing problem. Drug resistance to MTB arises due to the improper use of antibiotics in chemotherapy of drug-susceptible tuberculosis patients. This improper use is a result of a number of actions, including administration of improper treatment regimens by health care workers and failure to ensure that patients complete the whole course of treatment.

One group of compounds which has shown much promise for the treatment of tumors is the taxane group. Two prominent members of the taxane group are paclitaxel (Taxol) and docetaxel (Taxotere). Their structures are shown below:

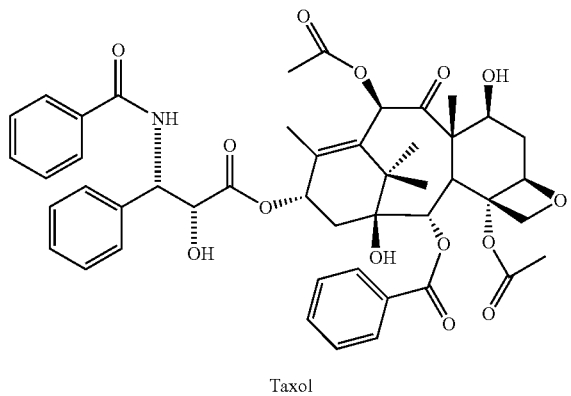

Taxol

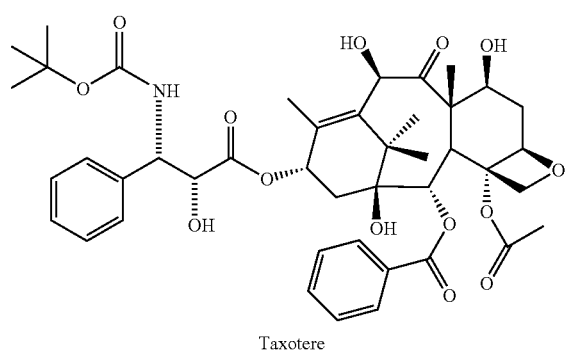

Taxotere

For example, a taxane derivative identified in Taraboletti et al., *Clin. Canc. Res.* Vol. 8, 1182-88, April 2002, as possessing antiangiogenic and antitumor activity is IDN 5390:

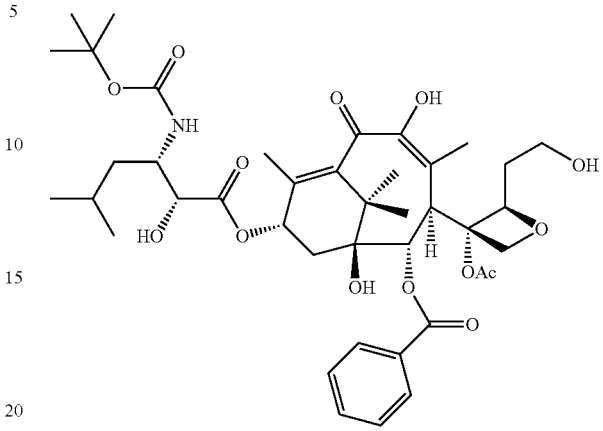

IDN 5390

However, taxanes have not previously been shown to possess anti-tuberculosis activity. Accordingly, there is a need for the development of novel anti-tuberculosis taxanes that are effective against both sensitive and resistant MTB strains.

SUMMARY OF THE INVENTION

The present invention relates to compounds that are effective against both sensitive and resistant MTB strains. In one embodiment, the compounds have the structure shown in formula (I):

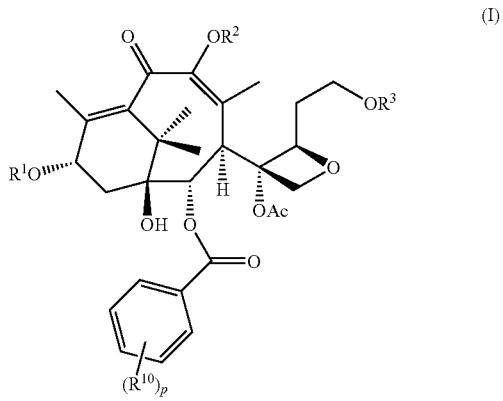

(I)

wherein:
$R^1$ represents Ar—C($R^4$)═C($R^5$)—CO—
Ar is a carbocyclic aromatic ring or fused ring system having 6 to 20 carbon atoms or a heterocyclic aromatic ring or fused ring system having 4 to 20 carbon atoms and at least one of S, O, N, or HN, wherein the carbocyclic aromatic ring or fused ring system or the heterocyclic aromatic or fused ring system is unsubstituted, or is substituted at any position with one or more substituents selected from the group consisting of $R^6$, $R^7$, $R^8$, and $Ar^1$;
$R^2$ and $R^3$ are the same or different and each is selected from the group consisting of $R^9$, C(O)$R^9$, C(O)O$R^9$, C(O)O$Ar^1$, C(O)$Ar^1$, C(O)N($Ar^1$)$_2$, C(O)N$R^9Ar^1$, C(O)N($R^9$)$_2$, and C(O)(CH$_2$)$_n$N($R^9$)$_2$;
$R^4$ and $R^5$ are the same or different and each is selected from the group consisting of $R^9$, $Ar^1$, O$Ar^1$, halo, O$R^9$, S$R^9$, N($R^9$)$_2$, OC(O)$R^9$, $R^9$NC(O)$R^9$, OC(O)N($R^9$)$_2$, $R^9$NC(O)O$R^9$, N($Ar^1$)$_2$, N$R^9Ar^1$, $R^9$NC(O)$Ar^1$, OC(O)N($Ar^1$)$_2$, $R^9$NC(O)O$Ar^1$, $Ar^1$NC(O)$R^9$, $Ar^1$NC(O)O$R^9$, $Ar^1$NC(O)$Ar^1$, and $Ar^1$NC(O)O$Ar^1$;

R⁶ in each occurrence may be the same or different, and represents an alkyl group having 1-6 carbon atoms.

R⁷ in each occurrence may be the same or different and is selected from the group consisting of halo, nitro, (R⁹)₂N, R⁹—S, R⁹—O, (Ar²)₂N, Ar²—NR⁹, Ar²—S, and Ar²—O;

R⁸ in each occurrence may be the same or different, and is selected from the group consisting of X—R⁹ and X—Ar², wherein X is selected from the group consisting of C(O)—, OC(O)—, C(O)O—, OC(O)O—, R⁹NC(O)—, C(O)NR⁹—, OC(O)NR⁹, R⁹NC(O)O—,; Ar²NC(O)—; C(O)NAr²—, OC(O)NAr² and Ar²NC(O)O—;

R⁹ in each occurrence may be the same or different and is selected from the group consisting of hydrogen and an alkyl group having 1-20 carbon atoms, wherein the alkyl group may be unsubstituted or substituted at any position with one or more substituents of R¹¹;

R¹⁰ in each occurrence may be the same or different, may occur at any position, and is selected from the group consisting of halo, nitro, R⁶, R⁶—O, HO, (R⁶)₂N, R⁶NH, NH₂, R⁶S, HS, CN, and N₃;

R¹¹ in each occurrence may be the same or different and is selected from the group consisting of halo, nitro, R⁶, CN, N₃, (R⁶)₂N, HNR⁶, NH₂, R⁶—S, HS, R⁶—O, HO, (Ar²)₂N, Ar²—NR⁶, Ar²—NH, Ar²—S, and Ar²—O;

Ar¹ in each occurrence may be the same or different, and is a carbocyclic aromatic ring or fused ring system having 6 to 20 carbon atoms or a heterocyclic aromatic ring or fused ring system having 4 to 20 carbon atoms and at least one of S, O, N, or HN, wherein the carbocyclic aromatic ring or fused ring system or the heterocyclic aromatic ring or fused ring system is unsubstituted or is substituted at any position with one or more substituent selected from the group consisting of R⁶, R⁷, R⁸, and Ar²;

Ar² in each occurrence may be the same or different, and is a carbocyclic aromatic ring or fused ring system having 6 to 20 carbon atoms or a heterocyclic aromatic ring or fused ring system having 4 to 20 carbon atoms and at least one of S, O, N, or HN, wherein the carbocyclic aromatic ring or fused ring system or the heterocyclic aromatic ring or fused ring system is unsubstituted or is substituted at any position with one or more substituents of R¹⁰;

n is 1 to 3; and p is 0 to 5, with the provision that R¹⁰ in each occurrence may be the same or different when p is greater that 1.

In one embodiment, the inventive compounds have the structure shown in formula (II):

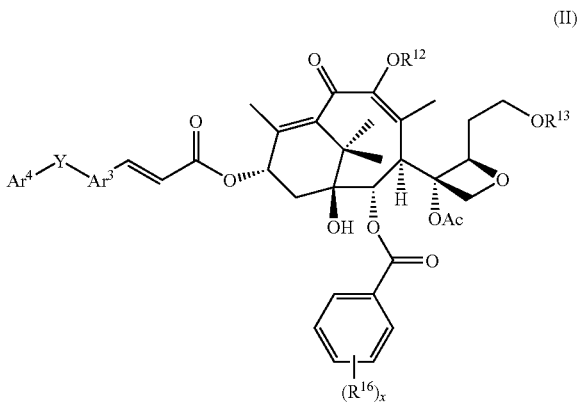

(II)

wherein

Ar³ is a divalent carbocyclic aromatic ring or fused ring system having 6 to 20 carbon atoms or a heterocyclic aromatic ring or fused ring system having 4 to 10 carbon atoms and at least one of S, O, N, or HN, wherein the carbocyclic aromatic ring or fused ring system or the heterocyclic aromatic ring or fused ring system is unsubstituted or substituted at any position with one or more substituents selected from the group consisting of halo, phenoxy, phenyl, methoxy, ethoxy, methyl, ethyl, NH₂, dimethylamino, and diethylamino;

Ar⁴ is a carbocyclic aromatic ring or fused ring system having 6 to 20 carbon atoms or a heterocyclic aromatic ring or fused ring system having 4 to 10 carbon atoms and at least one of S, O, N, or HN, wherein the carbocyclic aromatic ring or fused ring system or the heterocyclic aromatic ring or fused ring system is unsubstituted or is substituted at any position with one or more substituents selected from the group consisting of halo, phenoxy, phenyl, methoxy, ethoxy, methyl, ethyl, NH₂, dimethylamino, and diethylamino;

Y is selected from the group consisting of O, S, NH, and NR¹⁵;

R¹² and R¹³ are the same or different and each is selected from the group consisting of H, R¹⁵, C(O)R¹⁵, C(O)OR¹⁵, C(O)OAr³, C(O)Ar³, and C(O)(CH₂)ₙN(R¹⁵)₂;

R¹⁵ is an alkyl group having 1 to 4 carbon atoms;

R¹⁶ in each occurrence may be the same or different, may occur at any position, and is selected from the group consisting of halo, nitro, R¹⁵R¹⁵—O, HO, (R¹⁵)₂N, R¹⁵NH, NH₂, R¹⁵S, HS, CN, and N₃;

k in 0 to 5, with the provision that R¹⁶ in each occurrence may be the same or different when k is greater that 1; and n is 1 to 3.

In another embodiment, the inventive compounds have the structure shown in formula (III):

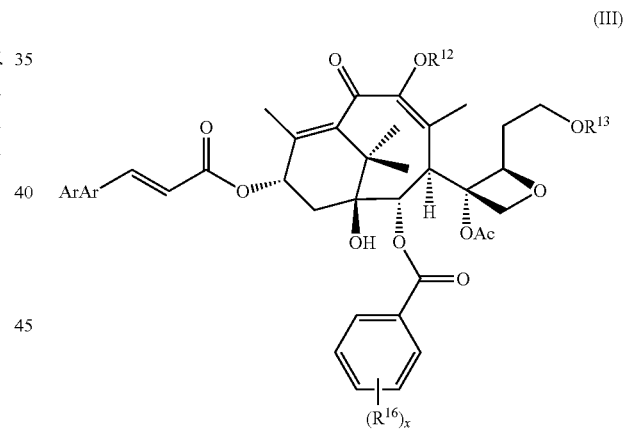

(III)

wherein

ArAr is a carbocyclic aromatic ring or fused ring system having 10-20 carbon atoms or a heterocyclic fused ring system having 8-20 carbon atoms and at least one of S, O, N, or HN, wherein the carbocyclic aromatic fused ring system or the heterocyclic aromatic fused ring system is unsubstituted or substituted with one or more substituents selected from the group consisting of halo, nitro, R¹⁵, R¹⁵—O, HO, (R¹⁵)₂N, R¹⁵NH, NH₂, R¹⁵S, and HS;

R¹² and R¹³ are the same or different and each is selected from the group consisting of H, R¹⁵, C(O)R¹⁵, C(O)OR¹⁵, C(O)OAr³, C(O)Ar³, and C(O)(CH₂)ₙN(R¹⁵)₂;

R¹⁵ is an alkyl group having 1 to 4 carbon atoms; and

R¹⁶ in each occurrence may be the same or different, may occur at any position, and is selected from the group consisting of halo, nitro, R¹⁵R¹⁵—O, HO, (R¹⁵)₂N, R¹⁵NH, NH₂, R¹⁵S, HS, CN, and N₃;

k in each occurrence may be the same or different, and is 0 to 5, with the provision that $R^{16}$ in each occurrence may be the same or different when k is greater than 1; and n is 1 to 3.

DETAILED DESCRIPTION OF THE INVENTION the term "alkyl" in each occurrence is intended to refer to saturated hydrocarbon groups of the designated number of carbon atoms, of a straight, branched, cyclic configuration, or a combination thereof. Examples of alkyl include methyl, ethyl, propyl, butyl, sec- and tert-butyl, pentyl, hexyl, heptyl, cyclopropyl, cyclobutyl, cyclopentyl, cyclohexyl, cycloheptyl, norbornyl, and the like.

The term "carbocyclic aromatic ring" is intended to refer to any stable monocyclic ring of 6 to 10 ring atoms, wherein the ring is aromatic. An example of a carbocyclic aromatic ring is phenyl.

The term "carbocyclic aromatic fused ring system" is intended to refer to bicyclic or tricyclic carbon ring of 8 to 20 ring atoms, wherein at least one ring is aromatic. Examples of a carbocyclic aromatic fused ring system include naphthyl, dihydro-naphthyl, indanyl, biphenyl, phenanthryl, anthryl, and acenaphthyl. In cases where the aryl substituent if bicyclic and one ring is non-aromatic, it is understood that attachment to the rest of the molecule is via the aromatic ring.

The term "heterocyclic aromatic ring" is intended to refer to a stable monocyclic ring of 5 to 10 ring atoms, wherein the ring is aromatic and contains from 1 to 4 heteroatoms selected from S, O, N, or HN. Examples of a heterocyclic aromatic ring include, furanyl, isothiazoly, isoxazoly, oxadiazolyl, oxazolyl, oxazoline, isoxazoline, oxetanyl, pyranyl, pyrazinyl, pyrazolyl, pyridazinyl, pyridazinyl, pyridyl, pyrimidyl, pyrrolyl, tetrazolyl, thiadiazolyl, thizaolyl, thienyl, triazolyl, azetidinyl, dihydroisooxazolyl, dihydroisothiazolyl, dihydrooxadiazolyl, dihydrooxazolyl, dihydrophrazinyl, dihydropyrazolyl, dihydropyridinyl, dihydropyrimidinyl, dihydropyrrolyl, dihydrotetrazolyl, dihydrothiadiazolyl, dihydrothiazolyl, dihydrothienyl, dihydrotriazolyl, dihydroazetidinyl, tetrahydrothienyl, pyrrazolyl, isoxazolyl, isothiazolyl, and pyridinyl.

The term "heterocyclic aromatic fused ring system" is intended to refer to bicyclic or tricyclic rings of 7 to 20 ring atoms, wherein at least one ring is aromatic and contains from 1 to 4 heteroatoms. In cases where the heteroaryl substituent is bicyclic and one ring is non-aromatic or contains no heteroatoms, it is understood that attachment is via the aromatic ring or via the heteroatom containing ring, respectively. If the heteroaryl ring contains nitrogen atoms, it is understood that the corresponding N-oxides thereof are also encompassed by this definition. Examples of a heterocyclic aromatic fused ring system include carbolinyl, benzoimidazolyl, benzofuranyl, benzofurazanyl, benzopyrazolyl, benzotriazolyl, benzothiophenyl, benzoxazolyl, carbazolyl, cinnolinyl, indolinyl, indolyl, indolazinyl, indazolyl, isobenzofuranyl, isoindolyl, isoquinolyl, napthpyridinyl, quinazolinyl, quinolyl, quinoxalinyl, tetrazolopyridyl, dihydrobenzoimidazolyl, dihydrobenzofuranyl, dihydrobenzothiophenyl, dihydrobenzoxazolyl, dihydroindolyl, dihydroquinolinyl, methylenedioxybenzoyl, cinnolinyl, quinoxalinyl, indolyl, benzotriazolyl, benzothiazolyl, benzoxazolyl, benzothienyl, quinolinyl, isoquinolinyl, tetra-hydroquinoline, acridinyl, carbazolyl, and phenanthridinyl.

The term "halo" or "halogen" is intended to include the atoms fluorine, chlorine, bromine, and iodine.

Compounds of the Invention

The compounds of the present invention are useful for treating subjects who are infected with *Mycobacterium tuberculosis*. In one embodiment of the present invention, compounds useful for such subjects include compounds of formula (I):

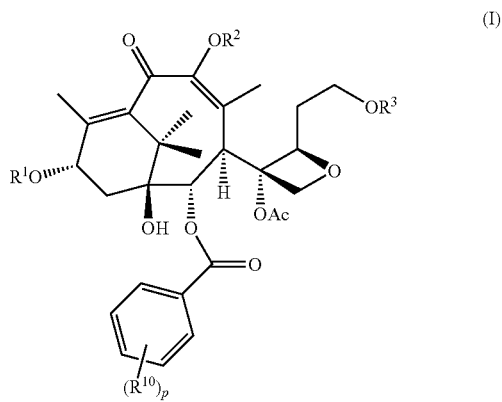

(I)

$R^1$ represents $Ar—C(R^4)=C(R^5)—CO—$

Ar is a carbocyclic aromatic ring or fused ring system having 6 to 20 carbon atoms or a heterocyclic aromatic ring or fused ring system having 4 to 20 carbon atoms and at least one of S, O, N, or HN, wherein the carbocyclic aromatic ring or fused ring system or the heterocyclic aromatic or fused ring system is unsubstituted, or is substituted at any position with one or more substituents selected from the group consisting of $R^6$, $R^7$, $R^8$, and $Ar^1$. In a preferred embodiment, the substituted or unsubstituted carbocyclic aromatic ring or fused ring system has 6 to 10 carbon atoms, and the substituted or unsubsubstituted heterocyclic aromatic ring fused system has 4 to 10 carbon atoms.

$R^2$ and $R^3$ are the same or different and each is selected from the group consisting of $R^9$, $C(O)R^9$, $C(O)OR^9$, $C(O)OAr^1$, $C(O)Ar^1$, $C(O)N(Ar^1)_2$, $C(O)NR^9Ar^1$, $C(O)N(R^9)_2$, and $C(O)(CH_{2n}N(R^9)_2$. In a preferred embodiment, $R^2$ and $R^3$ are each selected from the group consisting of H, $C(O)R^9$, $C(O)Ar^1$, and $C(O)(CH_2)_nN(R^9)_2$;

$R^4$ and $R^5$ are the same or different and each is selected from the group consisting of $R^9$, $Ar^1$, $OAr^1$, halo, $OR^9$, $SR^9$, $N(R^9_2$, $OC(O)R^9$, $R^9NC(O)R^9$, $OC(O)N(R^9)_2$, $R^9NC(O)OR^9$, $N(Ar^1)_2$, $NR^9Ar^1$, $R^9NC(O)Ar^1$, $OC(O)N(Ar^1)_2$, $R^9NC(O)OAr^1$, $Ar^1NC(O)R^9$, $Ar^1NC(O)OR^9$, $Ar^1NC(O)Ar^1$, and $Ar^1NC(O)OAr^1$. In a preferred embodiment, $R^4$ and $R^5$ are each selected from the group consisting of $R^9$, $Ar^1$, $OAr^1$, halo, $OR^9$, $N(R^9)_2$, $OC(O)R^9$, $R^9NC(O)R^9$, $N(Ar^1)_2$, $NR^9Ar^1$, $R^9NC(O)Ar^1$, $Ar^1NC(O)R^9$, and $Ar^1NC(O)Ar^1$.

$R^6$ in each occurrence maybe the same or different and represent an alkyl group having 1-6 carbon atoms. In a preferred embodiment, $R^6$ has 1 to 4 carbon atoms. In a more preferred embodiment, $R^6$ has 1 or 2 carbon atoms.

$R^7$ in each occurrence may be the same of different and is selected from the group consisting of halo, nitro, $(R^9)_2N$, $R^9—S$, $R^9—O$, $(Ar^2)_2N$, $Ar^2—Nr^9$, $Ar^2—S$, and $Ar^2—O$. In a preferred embodiment, $R^7$ is selected from the group consisting of halo, $(R^9)_2N$, $R^9—O$, $(Ar^2)_2N$, $Ar^2—NR^9$, and $Ar^2—O$.

$R^8$ in each occurrence may be the same or different, and is selected from the group consisting of $X—R^9$ and $X—Ar^2$, wherein X is selected from the group consisting of C(O)—, OC(O)—, C(O)O—, OC(O)O—, $R^9$NC(O)—, C(O)N$R^9$—, OC(O)N$R^9$, $R^9$NC(O)O—; $Ar^2$NC(O)—, C(O)NAr$^2$— and $Ar^2$NC(O)O—. In a preferred embodiment, X is selected from the group consisting of C(O)—, OC(O)—, C(O)O—, $R^9$NC(O)—, C(O)N$R^9$—, $Ar^2$NC(O)—, and C(O)NAr$^2$—.

$R^9$ in each occurrence may be the same or different and is selected from the group consisting of hydrogen and an alkyl group having 1-20 carbon atoms, wherein the alkyl group may be unsubstituted or substituted at any position with one or more substituents of $R^{11}$. In a preferred embodiment, $R^9$ is selected from the group consisting of H and an alkyl group having 1 to 4 carbon atoms, wherein the alkyl group may be unsubstituted or substituted at any position with one or more substituents of $R^{11}$.

$R^{10}$ in each occurrence may be the same or different, may occur at any position, and is selected from the group consisting of halo, nitro, $R^6$, $R^6$—O, HO, $(R^6)_2$N, $R^6$NH, NH$_2$, $R^6$S, HS, CN, and N$_3$. In a preferred embodiment, $R^{10}$ is selected from the group consisting of halo, $R^6$, $R^6$—O, HO, $(R^6)_2$N, $R^6$NH, and NH$_2$.

$R^{11}$ in each occurrence may be the same or different and is selected from the group consisting of halo, nitro, $R^6$, CN, N$_3$, $(R^6)_2$N, HNR$^6$, NH$_2$, $R^6$—S, HS, $R^6$—O, HO, $(Ar^2)_2$N, $Ar^2$—NR$^6$, $Ar^2$—NH, $Ar^2$—S, and $Ar^2$—O. In a preferred embodiment, $R^{11}$ is selected from the group consisting of halo, $(R^6)_2$N, HNR$^6$, NH$_2$, $R^6$—O, HO, $(Ar^2)_2$N, $Ar^2$—NR$^6$, $Ar^2$—NH, and $Ar^2$—O.

$Ar^1$ in each occurrence may be the same or different, and is a carbocyclic aromatic ring or fused ring system having 6 to 20 carbon atoms or a heterocyclic aromatic ring or fused ring system having 4 to 20 carbonatoms and at least one of S, O, N, ir HN, wherein the carbocyclic aromatic ring or fused ring system or the heterocyclic aromatic ring or fused ring system is unsubstituted or is substituted at any position with one or more substituent selected from the group consisting of $R^6$, $R^7$, $R^8$, and $Ar^2$. In a preferred embodiment, the substituted or unsubsubstituted carbocyclic aromatic ring or fused ring system has 6 to 10 carbon atoms, and the substituted or unsubsubstituted heterocyclic aromatic ring fused system has 4 to 10 carbon atoms.

$Ar^2$ in each occurrence may be the same or different, and is a carbocyclic aromatic ring or fused ring system having 6 to 20 carbon atoms or a heterocyclic aromatic ring or fused ring system having 4 to 20 carbon atoms and at least one of S, O, N, or HN, wherein the carbocyclic aromatic ring or fused ring system or the hterocyclic aromatic ring or fused ring system is unsubstituted or is substituted at any position with one or more substituents of $R^{10}$. In a preferred embodiment, the substituted or unsubsubstituted carbocyclic aromatic ring or fused ring system has 6 to 10 carbon atoms, and the substituted or unsubsubstituted heterocyclic aromatic ring fused system has 4 to 10 carbon atoms.

n is 1 to 3. In a preferred embodiment, n is 2. In a more preferred embodiment, n is 1.

p is 0 to 5, with the provision that $R^{10}$ in each occurrence may be the same or different when p is greater than 1. In a preferred embodiment, p is 1 to 3. In a more preferred embodiment, p is 1 to 2. In an even more preferred embodiment, p is 1.

In one embodiment of the compound of formula (I):

Ar is a carbocyclic aromatic ring or fused ring system having 6 to 10 carbon atoms or a heterocyclic aromatic ring or fused ring system having 4 to 10 carbon atoms and at least one of S, O, N, or HN, wherein the carbocyclic aromatic ring or fused ring system or the heterocyclic aromatic or fused ring system is unsubstituted, or is substituted at any position with one or more substituents selected from the group consisting of $R^6$, $R^7$, $R^8$, and $Ar^1$;

$Ar^1$ is a carbocyclic aromatic ring or fused ring system having 6 to 10 carbon atoms or a heterocyclic aromatic ring or fused ring system having 4 to 10 carbon atoms and at least one of S, O, N, or HN, wherein the carbocyclic aromatic ring or fused ring system or the heterocyclic aromatic or fused ring system is unsubstituted, or is substituted at any position with one or more substituents selected from the group consisting of $R^6$, $R^7$, $R^8$, and $Ar^2$;

$Ar^2$ is a carbocyclic aromatic ring or fused ring system having 6 to 10 carbon atoms or a heterocyclic aromatic ring or fused ring system having 4 to 10 carbon atoms and at least one of S, O, N, or HN, wherein the carbocyclic aromatic ring or fused ring system or the heterocyclic aromatic or fused ring system is unsubstituted, or is substituted at any position with one or more substituents of $R^{10}$;

$R^6$ is an alkyl group having 1 to 4 carbon atoms;

$R^7$ is selected from the group consisting of halo, $(R^9)_2$N, $R^9$—O, $(Ar^2)_2$N, $Ar^2$—NR$^9$, and $Ar^2$—O;

$R^8$ is selected from the group consisting of X—$R^9$ and X—$Ar^2$, wherein X is selected from the group consisting of C(O)—, OC(O)—, C(O)O—, $R^9$NC(O)—, C(O)N$R^9$—, $Ar^2$NC(O)—, and C(O)NAr$^2$—;

$R^9$ is selected from the group consisting of H and an alkyl group having 1 to 4 carbon atoms, wherein the alkyl group may be unsubstituted or substituted at any position with one or more substituents of $R^{11}$, and $R^{10}$ is selected from the group consisting of halo, $R^6$, $R^6$—O, HO, $(R^6)_2$N, $R^6$NH, and NH$_2$; and $R^{11}$ is selected from the group consisting of halo, $(R^6)_2$N, HNR$^6$, NH$_2$, $R^6$—O, HO, $(Ar^2)_2$N, $Ar^2$—NR$^6$, $Ar^2$—NH, and $Ar^2$—O.

In another embodiment, the compound of formula (I):

$Ar^1$ is a carbocyclic aromatic ring or fused ring system having 6 to 10 carbon atoms or a heterocyclic aromatic ring or fused ring system having 4 to 10 carbon atoms and at least one of S, O, N, or HN, wherein the carbocyclic aromatic ring or fused ring system or the heterocyclic aromatic or fused ring system is unsubstituted or substituted at any position with one or more substituents selected from the group consisting of $R^6$, $R^7$, $R^8$, and $Ar^2$;

$Ar^2$ is a carbocyclic aromatic ring or fused ring system having 6 to 10 carbon atoms or a heterocyclic aromatic ring or fused ring system having 4 to 10 carbon atoms and at least one of S, O, N, or HN, wherein the carbocyclic aromatic ring or fused ring system or the heterocyclic aromatic or fused ring system is unsubstituted or substituted at any position with one or more substituents of $R^{10}$;

$R^6$ is an alkyl group having 1 to 4 carbon atoms;

$R^7$ is selected from the group consisting of halo, $(R^9)_2$N, $R^9$—O, $(Ar^2)_2$N, $Ar^2$—NR$^9$, and $Ar^2$—O;

$R^8$ is selected from the group consisting of X—$R^9$ and X—$Ar^2$, wherein X is selected from the group consisting of C(O)—, OC(O)—, C(O)O—, $R^9$NC(O)—, C(O)N$R^9$—, $Ar^2$NC(O)—, and C(O)NAr$^2$—;

$R^9$ is selected from the group consisting of H and an alkyl group having 1 to 4 carbon atoms, wherein the alkyl group may be unsubstituted or substituted at any position with one or more substituents of $R^{11}$; and $R^{10}$ is selected from the group consisting of halo, $R^6$, $R^6$—O, HO, $(R^6)_2$N, $R^6$NH, and NH$_2$; and $R^{11}$ is selected from the group consisting of halo, $(R^6)_2$N, HNR$^6$, NH$_2$, $R^6$—O, HO, $(Ar^2)_2$N, $Ar^2$—NR$^6$, $Ar^2$—NH, and $Ar^2$—O.

In still another embodiment of the compound of formula (I):

$Ar^2$ is a carbocyclic aromatic ring or fused ring system having 6 to 10 carbon atoms or a heterocyclic aromatic ring or fused ring system having 4 to 10 carbon atoms and at least one of S, O, N, or HN, wherein the carbocyclic aromatic ring or fused ring system or the heterocyclic aromatic or fused ring system is unsubstituted, or is substituted at any position with one or more substituents of $R^{10}$;

$R^6$ is an alkyl group having 1 to 4 carbon atoms; and $R^{10}$ is selected from the group consisting of halo, $R^6$, $R^6$—O, HO, $(R^6)_2N$, $R^6NH$, and $NH_2$.

In yet another embodiment of the compound of formula (I):

$R^2$ and $R^3$ are selected from the group consisting of H, C(O)$R^9$, $C(O)Ar^1$, and $C(O)(CH_2)_nN(R^9)_2$;

$Ar^1$ is a carbocyclic aromatic ring or fused ring system having 6 to 10 carbon atoms or a heterocyclic aromatic ring or fused ring system having 4 to 10 carbon atoms and at least one of S, O, N, or HN, wherein the carbocyclic aromatic ring or fused ring system or the heterocyclic aromatic or fused ring system is unsubstituted or substituted at any position with one or more substituents selected from the group consisting of $R^6$, $R^7$, $R^8$, and $Ar^2$;

$Ar^2$ is a carbocyclic aromatic ring or fused ring system having 6 to 10 carbon atoms or a heterocyclic aromatic ring or fused ring system having 4 to 10 carbon atoms and at least one of S, O, N, or HN, wherein the carbocyclic aromatic ring or fused ring system or the heterocyclic aromatic or fused ring system is unsubstituted or is substituted at any position with one or more substituents of $R^{10}$;

$R^6$ is an alkyl group having 1 4 carbon atoms;

$R^7$ is selected from the group consisting of halo, $(R^9)_2N$, $R^9$—O, $(Ar^2)_2N$, $Ar^2$—$NR^9$, and $Ar^2$—O;

$R^8$ is selected from the group consisting of X—$R^9$ and X—$Ar^2$, wherein X is selected from the group consisting of C(O)—, OC(O)—, C(O)O—, $R^9NC(O)$—, $C(O)NR^9$—, $Ar^2NC(O)$—, and $C(O)NAr^2$—;

$R^9$ is selected from the group consisting of H and an alkyl group having 1 to 4 carbon atoms, wherein the alkyl group may be unsubstituted or substituted at any position with one or more substituents of $R^{11}$; and $R^{10}$ is selected from the group consisting of halo, $R^6$, $R^6$—O, HO, $(R^6)_2N$, $R^6NH$, and $NH_2$;

$R^{11}$ is selected from the group consisting of halo, $(R^6)_2N$, $HNR^6$, $NH^2$, $R^6$—O, HO, $(Ar^2)_2N$, $Ar^2$—$NR^6$, $Ar^2$—NH, and $Ar^2$—O; and n is 1 to 3.

In a further embodiment of the compound of formula (I):

$R^4$ and $R^5$ are each selected from the group consisting of $R^9$, $Ar^1$, $OAr^1$, halo, $OR^9$, $N(R^9)_2$, $OC(O)R^9$, $R^9NC(O)R^9$, $N(Ar^1)_2$, $NR^9Ar^1$, $R^9NC(O)Ar^1$, $Ar^1NC(O)R^9$, and $Ar^1NC(O)Ar^1$;

$Ar^1$ is a carbocyclic aromatic ring or fused ring system having 6 to 10 carbon atoms or a heterocyclic aromatic ring or fused ring system having 4 to 10 carbon atoms and at least one of S, O, N, or HN, wherein the carbocyclic aromatic ring or fused ring system or the heterocyclic aromatic or fused ring system is unsubstituted or substituted at any position with one or more substituents selected from the group consisting of $R^6$, $R^7$, $R^8$, and $Ar^2$;

$Ar^2$ is a carbocyclic aromatic ring or fused ring system having 6 to 10 carbon atoms or a heterocyclic aromatic ring or fused ring system having 4 to 10 carbon atoms and at least one of S, O, N, or HN, wherein the carbocyclic aromatic ring or fused ring system or the heterocyclic aromatic or fused ring system is unsubstituted or substituted at any position with one or more substituents selected of $R^{10}$;

$R^6$ is an alkyl group having 1 4 carbon atoms;

$R^7$ is selected from the group consisting of halo, $(R^9)_2N$, $R^9$—O, $(Ar^2)_2N$, $Ar^2$—$NR^9$, and $Ar^2$—O;

$R^8$ is selected from the group consisting of X—$R^9$ and X—$Ar^2$, wherein X is selected from the group consisting of C(O)—, OC(O)—, C(O)O—, $R^9NC(O)$—, $C(O)NR^9$—, $Ar^2NC(O)$—, and $C(O)NAr^2$—;

$R^9$ is selected from the group consisting of H and an alkyl group having 1 to 4 carbon atoms, wherein the alkyl group may be unsubstituted or substituted at any position with one or more substituents of $R^{11}$;

$R^{10}$ is selected from the group consisting of halo, $R^6$, $R^6$—O, HO, $(R^6)_2N$, $R^6NH$, and $NH_2$; and $R^{11}$ is selected from the group consisting of halo, $(R^6)_2N$, $HNR^6$, $NH^2$, $R^6$—O, HO, $(Ar^2)_2N$, $Ar^2$—$NR^6$, $Ar^2$—NH, and $Ar^2$—O.

In yet a further embodiment of the compound of formula (I), $R^6$ is an alkyl group having 1 to 4 carbon atoms.

In still a further embodiment of the compound of formula (I):

$R^7$ is selected from the group consisting of halo, $(R^9)_2N$, $R^9$—O, $(Ar^2)_2N$, $Ar^2$—$NR^9$, and $Ar^2$—O;

$Ar^2$ is a carbocyclic aromatic ring or fused ring system having 6 to 10 carbon atoms or a heterocyclic aromatic ring or fused ring system having 4 to 10 carbon atoms and at least one of S, O, N, or HN, wherein the carbocyclic aromatic ring or fused ring system or the heterocyclic aromatic or fused ring system is unsubstituted or is substituted at any position with one or more substituents of $R^{10}$;

$R^6$ is an alkyl group having 1 to 4 carbon atoms;

$R^9$ is selected from the group consisting of H and an alkyl group having 1 to 4 carbon atoms, wherein the alkyl group may be unsubstituted or substituted at any position with one or more substituents of $R^{11}$;

$R^{10}$ is selected from the group consisting of halo, $R^6$, $R^6$—O, HO, $(R^6)_2N$, $R^6NH$, and $NH_2$; and $R^{11}$ is selected from the group consisting of halo, $(R^6)_2N$, $HNR^6$, $NH^2$, $R^6$—O, HO, $(Ar^2)_2N$, $Ar^2$—$NR^6$, $Ar^2$—NH, and $Ar^2$—O.

In still another embodiment of the compound of formula (I):

$R^8$ is selected from the group consisting of X—$R^9$ and X—$Ar^2$, wherein X is selected from the group consisting of C(O)—, OC(O)—, C(O)O—, $R^9NC(O)$—, $C(O)NR^9$—, $Ar^2NC(O)$—, and $C(O)NAr^2$—;

$Ar^2$ is a carbocyclic aromatic ring or fused ring system having 6 to 10 carbon atoms or a heterocyclic aromatic ring or fused ring system having 4 to 10 carbon atoms and at least one of S, O, N, or HN, wherein the carbocyclic aromatic ring or fused ring system or the heterocyclic aromatic or fused ring system is unsubstituted, or is substituted at any position with one or more substituents of $R^{10}$;

$R^6$ is an alkyl group having 1 to 4 carbon atoms; and $R^9$ is selected from the group consisting of H and an alkyl group having 1 to 4 carbon atoms, wherein the alkyl group may be unsubstituted or substituted at any position with one or more substituents of $R^{11}$;

$R^{10}$ is selected from the group consisting of halo, $R^6$, $R^6$—O, HO, $(R^6)_2N$, $R^6NH$, and $NH_2$; and $R^{11}$ is selected from the group consisting of halo, $(R^6)_2N$, $HNR^6$, $NH^2$, $R^6$—O, HO, $(Ar^2)_2N$, $Ar^2$—$NR^6$, $Ar^2$—NH, and $Ar^2$—O.

In yet another embodiment of the compound of formula (I):

$R^9$ is selected from the group consisting of H and an alkyl group having 1 to 4 carbon atoms, wherein the alkyl group may be unsubstituted or substituted at any position with one or more substituents of $R^{11}$;

$Ar^2$ is a carbocyclic aromatic ring or fused ring system having 6 to 10 carbon atoms or a heterocyclic aromatic ring or fused ring system having 4 to 10 carbon atoms and at least one of S, O, N, or HN, wherein the carbocyclic aromatic ring or fused ring system or the heterocyclic aromatic or fused ring system is unsubstituted, or is substituted at any position with one or more substituents of $R^{10}$;

$R^6$ is an alkyl group having 1 to 4 carbon atoms.

$R^{10}$ is selected from the group consisting of halo, $R^6$, $R^6$—O, HO, $(R^6)_2$N, $R^6$NH, and $NH_2$; and $R^{11}$ is selected from the group consisting of halo, $(R^6)_2$N, $HNR^6$, $NH_2$, $R^6$—O, HO, $(Ar^2)_2$—N, $Ar^2$—$NR^6$, $Ar^2$—NH, and $Ar^2$—O.

In still another embodiment of the compound of formula (I):

$R^{10}$ is selected from the group consisting of halo, $R^6$, $R^6$—O, HO, $(R^6)_2$N, $R^6$NH, and $NH_2$; and $R^6$ is an alkyl group having 1 to 4 carbon atoms.

In a further embodiment of the compound of formula (I):

$R^{11}$ is selected from the group consisting of halo, $(R^6)_2$N, $HNR^6$, $NH_2$, $R^6$—O, HO, $(Ar^2)_2$N, $Ar^2$—$NR^6$, $Ar^2$—NH, and $Ar^2$—O;

$Ar^2$ is a carbocyclic aromatic ring or fused ring system having 6 to 10 carbon atoms or a heterocyclic aromatic ring or fused ring system having 4 to 10 carbon atoms and at least one of S, O, N, or HN, wherein the carbocyclic aromatic ring or fused ring system or the heterocyclic aromatic or fused ring system is unsubstituted or is substituted at any position with one or more substituents of $R^{10}$;

$R^6$ is an alkyl group having 1 4 carbon atoms; and $R^{10}$ is selected from the group consisting of halo, $R^6$, $R^6$—O, HO, $(R^6)_2$N, $R^6$NH, and $NH_2$.

In yet a further embodiment of the compound of formula (I):

Ar is a carbocyclic aromatic ring or fused ring system having 6 to 10 carbon atoms or a heterocyclic aromatic ring or fused ring system having 4 to 10 carbon atoms and at least one of S, O, N, or HN, wherein the carbocyclic aromatic ring or fused ring system or the heterocyclic aromatic ring or fused ring system is unsubstituted or is substituted at any position with one or more substituents selected from the group consisting of $R^6$, $R^7$, $R^8$, and $Ar^1$;

$Ar^1$ is a carbocyclic aromatic ring or fused ring system having 6 to 10 carbon atoms or a heterocyclic aromatic ring or fused ring system having 4 to 10 carbon atoms and at least one of S, O, N, or HN, wherein the carbocyclic aromatic ring or fused ring system or the heterocyclic aromatic or fused ring system is unsubstituted or substituted at any position with one or more substituents selected from the group consisting of $R^6$, $R^7$, $R^8$, and $Ar^2$;

$Ar^2$ is a carbocyclic aromatic ring or fused ring system having 6 to 10 carbon atoms or a heterocyclic aromatic ring or fused ring system having 4 to 10 carbon atoms and at least one of S, O, N, or HN, wherein the carbocyclic aromatic ring or fused ring system or the heterocyclic aromatic or fused ring system is unsubstituted or substituted at any position with one or more substituents selected from the group consisting of $R^{10}$;

$R^2$ and $R^3$ are each selected from the group consisting of H, $C(O)R^9$, $C(O)OR^9$, $C(O)OAr^1$, and $C(O)Ar^1$, $C(O)N(Ar^1)_2$, $C(O)NR^9Ar^1$, $C(O)N(R^9)_2$, and $C(O)(CH_2)_n N(R^9)_2$;

$R^4$ and $R^5$ are each selected from the group consisting of $R^9$, $Ar^1$, $OAr^1$, halo, $OR^9$, $N(R^9)_2$, $OC(O)R^9$, $R^9NC(O)R^9$, $N(Ar^1)_2$, $NR^9Ar^1$, $R^9NC(O)Ar^1$, $Ar^1NC(O)R^9$, and $Ar^1NC(O)Ar^1$;

$R^6$ is an alkyl group having 1 to 4 carbon atoms;

$R^7$ is selected from the group consisting of halo, $(R^9)_2$N, $R^9$—O, $(Ar^2)_2$N, $Ar^2$—$NR^9$, and $Ar^2$—O;

$R^8$ is selected from the group consisting of X—$R^9$ and X—$Ar^2$, where X is selected from the group consisting of C(O)—, OC(O)—, C(O)O—, $R^9$NC(O)—, C(O)$NR^9$—, $Ar^2$NC(O)—, and C(O)$NAr^2$—;

$R^9$ is selected from the group consisting of H and an alkyl group having 1 to 4 carbon atoms, wherein the alkyl group may be unsubstituted or substituted at any position with one or more substituents of $R^{11}$;

$R^{10}$ is selected from the group consisting of halo, $R^6$, $R^6$—O, HO, $(R^6)_2$N, $R^6$NH, and $NH_2$;

$R^{11}$ is selected from the group consisting of halo $(R^6)_2$N, $HNR^6$, $NH_2$, $R^6$—O, HO, $(Ar^2)_2$N, $Ar^2$—$NR^6$, $Ar^2$—NH, and $Ar^2$—O; and n is 1 to 3.

In still a further embodiment of the compound of formula (I), Ar and $Ar^1$ may be the same or different, and each is a carbocyclic aromatic ring or fused ring system having 6 to 10 carbon atoms or a heterocyclic aromatic ring or fused ring system having 4 to 10 carbon atoms and at least one of S, O, N, or HN, wherein the carbocyclic aromatic ring or fused ring system or the heterocyclic aromatic ring or fused ring system is unsubstituted or substituted at any position with one or more substituents selected from the group consisting of halo, phenyl, methoxy, ethoxy, methyl ethyl, $NH_2$, dimethylamino, and diethylamino.

In another embodiment of the compound of formula (I):

$R^2$ and $R^3$ are each selected from the group consisting of H, $C(O)R^9$, $C(O)OR^9$, $C(O)OAr^1$, $C(O)Ar^1$, and $C(O)(CH_2)_n N(R^9)_2$;

$Ar^1$ is a carbocyclic aromatic ring or fused ring system having 6 to 10 carbon atoms or a heterocyclic aromatic ring or fused ring system having 4 to 10 carbon atoms and at least one of S, O, N, or HN, wherein the carbocyclic aromatic ring or fused ring system or the heterocyclic aromatic or fused ring system is unsubstituted or substituted at any position with one or more substituents selected from the group consisting of halo, phenoxy, phenyl, methoxy, ethoxy, methyl, ethyl, $NH_2$, dimethylamino, and diethylamino;

$R^9$ is selected from the group consisting of H and an alkyl group having 1 to 4 carbon atoms, wherein the alkyl group may be unsubstituted or substituted at any position with one or more substituents selected from the group consisting of halo, methoxy, ethoxy, $NH_2$, dimethylamino, and diethylamino; and n is 1 to 3.

In yet another embodiment of the compound of formula (I):

$R^4$ and $R^5$ are each selected from the group consisting of $R^9$, $Ar^1$, $OAr^1$, halo, $OR^9$, $N(R^9)_2$, $OC(O)R^9$, $R^9NC(O)R^9$, $N(Ar^1)_2$, $NR^9Ar^1$, $R^9NC(O)Ar^1$, $Ar^1NC(O)R^9$, and $Ar^1NC(O)Ar^1$;

$Ar^1$ is a carbocyclic aromatic ring or fused ring system having 6 to 10 carbon atoms or a heterocyclic aromatic ring or fused ring system having 4 to 10 carbon atoms and at least one of S, O, N, or HN, wherein the carbocyclic aromatic ring or fused ring system or the heterocyclic aromatic or fused ring system is unsubstituted or substituted at any position with one or more substituents selected from the group consisting of halo, phenyl, methoxy, ethoxy, methyl, ethyl, $NH_2$, dimethylamino, and diethylamino; and $R^9$ is selected from the group consisting of H and an alkyl group having 1 to 4 carbon atoms, wherein the alkyl group may be unsubstituted or substituted at any position with one or more substituents selected from the group consisting of halo, methoxy, ethoxy, NH$_2$, dimethylamino, and diethylamino; and In still another embodiment of the compound of formula (I), Ar and Ar$^1$ may be the same or different, and each is selected from the group consisting of phenyl, pyridyl, pyrimidinyl, naphthyl, quinolinyl, imidazolyl, triazolyl, thiophenyl, furanyl, indolyl, indolinyl, and pyrrolyl.

In a further embodiment of the compound of formula (I):
Ar and Ar$^1$ may be the same or different, and each is a carbocyclic aromatic ring or fused ring system having 6 to 10 carbon atoms or a heterocyclic aromatic ring or fused ring system having 4 to 10 carbon atoms and at least one of S, O, N, or HN, wherein the carbocyclic aromatic ring or fused ring system or the heterocyclic aromatic ring or fused ring system is unsubstituted or substituted at any position with one or more substituents selected from the group consisting of halo, phenyl, methoxy, ethoxy, methyl, ethyl, NH$_2$, dimethylamino, and diethylamino;
R$^2$ and R$^3$ are each selected from the group consisting of H, C(O)R$^9$, C(O)OR$^9$, C(O)OAr$^1$, C(O)Ar$^1$, and C(O)(CH$_2$)$_n$N(R$^9$)$_2$;
R$^4$ and R$^5$ are each selected from the group consisting of R$^9$, Ar$^1$, OAr$^1$, halo, OR$^9$, N(R$^9$)$_2$, OC(O)R$^9$, R$^9$NC(O)R$^9$, N(Ar$^1$)$_2$, NR$^9$Ar$^1$, R$^9$NC(O)Ar$^1$, Ar$^1$NC(O)R$^9$, and Ar$^1$NC(O)Ar$^1$;
R$^9$ is selected from the group consisting of H and an alkyl group having 1 to 4 carbon atoms, wherein the alkyl group may be unsubstituted or substituted at any position with one or more substituents selected from the group consisting of halo, methoxy, ethoxy, NH$_2$, dimethylamino, and diethylamino; and n is 1 to 3.

In yet another embodiment, the inventive compounds are of formula (I):

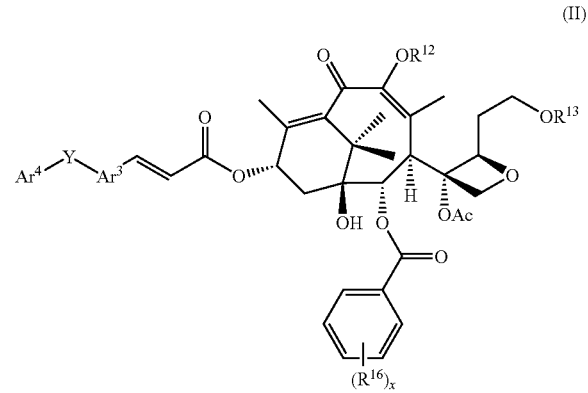

(II)

wherein
Ar$^3$ is a divalent carbocyclic aromatic ring or fused ring system having 6 to 10 carbon atoms or a heterocyclic aromatic ring or fused ring system having 4 to 10 carbon atoms and at least one of S, O, N, or HN, wherein the carbocyclic aromatic ring or fused ring system or the heterocyclic aromatic or fused ring system is unsubstituted or substituted at any position with one or more substituents selected from the group consisting of halo, phenyl, phenyl, methoxy, ethoxy, methyl, ethyl, NH$_2$, dimethylamino, and diethylamino;
Ar$^4$ is a carbocyclic aromatic ring or fused ring system having 6 to 10 carbon atoms or a heterocyclic aromatic ring or fused ring system having 4 to 10 carbon atoms and at least one of S, O, N, or HN, wherein the carbocyclic aromatic ring or fused ring system or the heterocyclic aromatic or fused ring system is unsubstituted or substituted at any position with one or more substituents selected from the group consisting of halo, phenoxy, phenyl, methoxy, ethoxy, methyl, ethyl, NH$_2$, dimethylamino, and diethylamino.
Y is selected from the group consisting of O, S, NH, and NR$^{15}$;
R$^{12}$ and R$^{13}$ are the same or different and each is selected from the group consisting of H, R$^{15}$, C(O)R$^{15}$, C(O)OR$^{15}$, C(O)OAr$^3$, C(O)Ar$^3$, and C(O)(CH$_2$)$_n$N(R$^{15}$)$_2$;
R$^{15}$ is an alkyl group having 1 to 4 carbon atoms;
R$^{16}$ in each occurrence may be the same or different, may occur at any position, and is selected from the group consisting of halo, nitro, R$^{15}$, R$^{15}$—O, HO, (R$^{15}$)$_2$N, R$^{15}$NH, NH$_2$, R$^{15}$S, HS, CN, and N$_3$;
k is 0 to 5, with the provision that R$^{16}$ in each occurrence may be the same or different when k is greater than 1; and
n it 1 to 3.

In another embodiment, the compound of formula (II) has the structure:

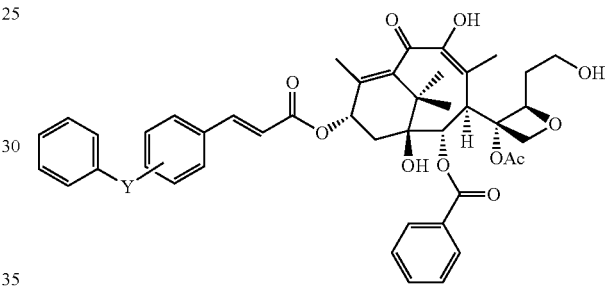

wherein Y is selected from the group consisting of O and S.

In yet another embodiment, the inventive compounds are of formula (III):

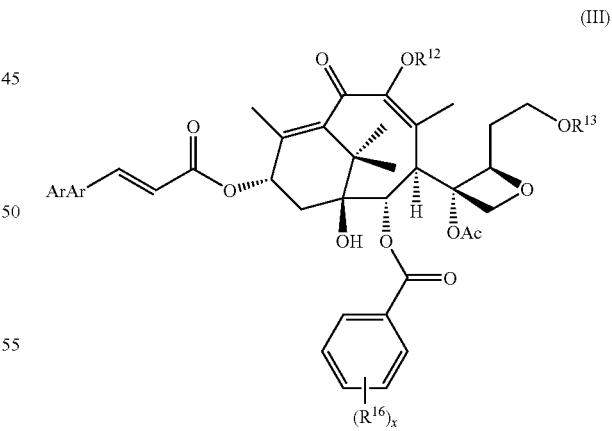

(III)

wherein
ArAr is a carbocyclic aromatic ring or fused ring system having 10-20 carbon atoms or a heterocyclic fused ring system having 8-20 carbon atoms and at least one of S, O, N, or HN, wherein the carbocyclic aromatic fused ring system or the heterocyclic aromatic fused ring system is unsubstituted or substituted with one or more substituents selected from the group consisting of halo, nitro, $R^{15}$, $R^{15}$—O, HO, $(R^{15})_2N$, $R^{15}NH$, $NH_2$, $R^{15}S$, and HS;

$R^{12}$ and $R^{13}$ are the same or different and each is selected from the group consisting of H, $R^{15}$, $C(O)R^{15}$, $C(O)OR^{15}$, $C(O)OAr^3$, $C(O)Ar^3$, and $C(O)(CH_2)_nN(R^{15})_2$;

$R^{15}$ is an alkyl group having 1 to 4 carbon atoms; and $R^{16}$ in each occurrence may be the same or different, may occur at any position, and is selected from the group consisting of halo, nitro, $R^{15}$, $R^{15}$—O, HO, $(R^{15})_2N$, $R^{15}NH$, $NH_2$, $R^{15}S$, HS, CN, and $N_3$;

k in each occurrence may be the same or different, and is 0 to 5, with the provision that $R^{16}$ in each occurrence may be the same or different when k is greater than 1; and n it 1 to 3.

In another embodiment, the compound of formula (III) has the structure:

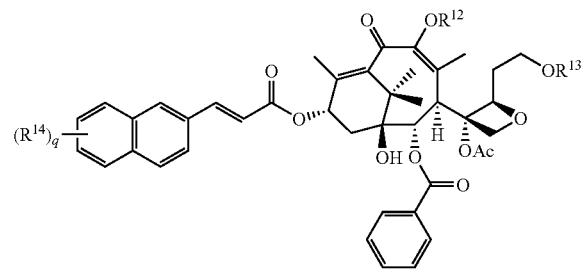

wherein $R^{14}$ is selected from the group consisting of halo, nitro, $R^{15}$, $R^{15}$—O, HO, $(R^{15})_2N$, $R^{15}NH$, and $NH_2$;

$R^{15}$ is an alkyl group having 1 to 4 carbon atoms; and q is 0 or 1.

In another embodiment, the present invention relates to a method for method for treating a patient infected with *Myobacterium tuberculosis*, the method comprising administering to the patient a compound of formula (I). In a preferred embodiment, the present invention relates to a method for treating a patient infected with *Myobacterium tuberculosis*, the method comprising administering to the patient a compound of formulas (II) or (III).

It is to be understood that the instant invention contemplates embodiments in which each group listed under one parameter (e.g. as a preferred embodiment), may be combined with all groups listed under any other parameter. For example, $R^6$ is identified hereinabove in a more preferred embodiment as having 1 to 2 carbon atoms, and $R^{10}$ is identified in a preferred embodiment as being selected from the group consisting of halo, $R^6$, $R^6$—O, HO, $(R^6)_2N$, $R^6NH$, and $NH_2$. Accordingly, in one embodiment of the present invention, $R^6$ has 1 or 2 carbon atoms, and $R^{10}$ is selected from the group consisting of halo, $R^6$, $R^6$—O, HO, $(R^6)_2N$, $R^6NH$, and $NH_2$.

Pharmaceutical Compositions and Methods of Use

The compounds of the present invention may have asymmetric centers and occur as racemates, racemic mixtures, and as individual diastereomers, with all possible isomers, including optical isomers, being included in the present invention. When any variable (e.g. $R^9$, $Ar^1$, etc.) occurs more than one time in any constituent, its definition on each occurence is independent at every other occurence. Also, combinations of substituents/or variables are permissible only if such combinations result in stable compounds.

The inventive compounds may be administered to the subject via any drug delivery route known in the art. Specific exemplary administration routes include oral, ocular, rectal, buccal, topical, nasal, opthamalic, subcutaneous, intramuscular, intravenous (bolus and infusion), intracerebral, transdermal and pulmonary.

The term "therapeutically effective amount", as used herein, refers to an amount of a pharmaceutical agent to treat, meliorate or prevent the identified disease or condition, or to exhibit a detectable therapeutic or inhibitory effect. The effect can be detected by, for example, assays disclosed in the following examples. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgement of the clinician.

For any compound, the therapeutically effective amount can be determined by a person having ordinary skill in the art. For example, the amount may be estimated initially either in cell culture assays, e.g., in animal models, such as rats, mice, rabbits, dogs, or pigs. The animal model may also be used to determine the appropriate concentration range and route of administration. Such information can then be used to determine useful doses and routes for administration in humans.

Therapeutic/prophylactic efficacy and toxicity may be determined by standard pharmaceutical procedures in cell cultures or experimental animals, e.g., $ED_{50}$ (the does therapeutically effective in 50% of the population) and $LD_{50}$ (the dose lethal to 50% of the population). The dose ratio between therapeutic and toxic effects is the therapeutic index, and it can be expressed as the ration, $ED_{50}/LD_{50}$. Pharmaceutical compositions that exhibit large therapeutic indices are preferred. The data obtained from cell culture assays and animal studies may be used in formulating a range of dosage for human use. The dosage contained in such compositions is preferably within a range of circulating concentrations that include an $ED_{50}$ with little or no toxicity. The dosage may vary within this range depending upon the dosage form employed, sensitivity of the patient, and the route of administration.

Guidance as to particular dosages and methods of delivery is provided in the literature and is generally available to practitioners in the art. In general the dose will be in the range of about 1 mg/day to about 1 g/day, or about 0.1 g to about 0.9 g/day, or about 0.3 g to about 0.8 g/day, or about 0.5 g to about 0.7 g/day, in single, divided, or continuous doses for a patient weighing between about 40 to about 100 kg (which dose may be adjusted for patients above or below this weight range, particularly children below 40 kg).

The exact dosage will be determined by the practitioner, in light of factors related to the subject that requires treatment. Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Pharmaceutically Acceptable Salts

The present invention also relates to pharmaceutically acceptable salts of the inventive compounds. The pharmaceutically acceptable salts of the compounds of this invention include the conventional non-toxic salts of the compounds of this invention as formed, e.g., from non-toxic inorganic or organic acids. For example, such conventional non-toxic salts include those derived from inorganic acids such as hydrochloric, hydrobromic, sulfuric sulfamic, phosphoric, nitric and the like: and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicyic, sulfanilic, 2-acetoxybenzoic, fumaric, toluenesulfonic, methanesulfonic, ethane disulfonic, oxalic, isethionic, trifluoroacetic and the like.

The pharmaceutically acceptable salts of the compounds of this invention can be synthesized from the compounds of this invention which contain a basic moiety by conventional chemical methods. Generally, the salts are prepared either by ion exchange chromatography or by reacting the free base with stoichiometric amounts or with a excess of the desired salt-forming inorganic or organic acid in a suitable solvent or various combinations of solvents.

Metabolites of the Compounds of the Invention

Also falling within the scope of the present invention are the in vivo metabolic products of the compounds described herein. Such products may result for example from the oxidation, reduction, hydrolysis, amidation, esterification and the like of the administered compound, primarily due to enzymatic processes. Accordingly, the invention includes compounds produced by a process comprising contacting a compound of this invention with a mammalian tissue or a mammal for a period of time sufficient to yield a metabolic product thereof. Such products typically are identified by preparing a radio-labeled (e.g. $C^{14}$ or $H^3$) compound of the invention, administering it in a detectable dose (e.g., greater than about 0.5 mg/kg) to a mammal such as rat, mouse, guinea pig, monkey, or to man, allowing sufficient time for metabolism to occur (typically about 30 seconds to 30 hours), and isolating its conversion products from urine, blood or other biological samples. These products are easily isolated since they are labeled (others are isolated by the use of antibodies capable of binding epitopes surviving in the metabolie). The metabolite structures are determined in conventional fashion, e.g., by MS or NMR analysis. In general, analysis of metabolites may be done in the same way as conventional drug metabolism studies will-known to those skilled in the art. The conversion products, so long as they are not otherwise found in vivo, are useful in diagnostic assays for therapeutic dosing of the compounds of the invention even if they possess no biological activity of their own.

Pharmaceutical Compositions of the Invention

While it is possible for the compounds of the present invention to be administered neat, it may be preferable to formulate the compounds as pharmaceutical compositions. As such, in yet another aspect of the invention, pharmaceutical compositions useful in the methods of the invention are provided. The pharmaceutical compositions of the invention may be formulated with pharmaceutically acceptable excipients such as carriers, solvents, stabilizers, adjuvants, diluents, etc., depending upon the particular mode of administration and dosage form. The pharmaceutical compositions should generall be formulated to achieve a physiologically compatible pH, and may range from a pH of about 3 to a pH of about 11, preferably about pH 3 to about pH 7, depending on the formulation and route of administration. In alternative embodiments, it may be preferred that the pH is adjusted to a range from about pH 5.0 to about pH 8.0

More particularly, the pharmaceutical compositions of the invention comprise a therapeutically or prophylactically effective amount of at least one compound of the present invention, together with one or more pharmaceutically acceptable excipients. Optionally, the pharmaceutical compositions of the invention may comprise a combination of compounds of the present invention, or may include a second active ingredient useful in the treatment of tuberculosis Formulations of the present invention, e.g., for parenteral or oral administration, are most typically solids, liquid solutions, emulsions or suspensions, while inhaleable formulations for pulmonary administration are generally liquids or powders, with powder formulations being generally preferred. A preferred pharmaceutical composition of the invention may also be formulated as a lyophilized solid that is reconstituted with a physiologically compatible solvent prior to administration. Alternative pharmaceutical compositions of the invention may be formulated as syrups, creams, ointments, tablets, and the like.

The term "pharmaceutically acceptable excipient" refers to an excipient for administration of a pharmaceutical agent, such as the compounds of the present invention. The term refers to any pharmaceutical excipient that may be administered without undue toxicity. Pharmaceutically acceptable excipients are determined in part by the particular composition being administered, as well as by particular method used to administer the composition. Accordingly, there exists a wide variety of suitable formulations of pharmaceutical compositions of the present invention (see e.g., Remington's Pharmaceutical Sciences).

Suitable excipients may be carrier molecules that include large, slowly metabolized macromolecules such as proteins, polysaccharides, polylactic acids, polyglycolic acids, polymeric amino acids, amino acid copolymers, and inactive virus particles. Other exemplary excipients include antioxidants such as ascorbic acid; chelating agents such as EDTA; carbohydrates such as dextrin, hydroxyalkylcellulose, hydroxyalkylmethylcellulose, stearic acid; liquids such as oils, water, saline, glycerol and ethanol; wetting or emulsifying agents; pH buffering substances; and the like. Liposomes are also included within the definition of pharmaceutically acceptable excipients.

The pharmaceutical compositions of the invention may be formulated in any form suitable for the intended method of administration. When intended for oral use for example, tablets, troches, lozenges, aqueous or oil suspensions, non-aqueous solutions, dispersible powders or granules (including micronized particles or nanoparticles), emulsions, hard or soft capsules, syrups or elixirs may be prepared. Compositions intended for oral use may be prepared according to any method known to the art for the manufacture of pharmaceutical compositions, and such compositions may contain one or more agents including sweetening agents, flavoring agents, coloring agents and preserving agents, in order to provide a palatable preparation.

Pharmaceutically acceptable excipients particularly suitable for use in conjunction with tablets include, for example, inert diluents, such as celluloses, calcium or sodium carbonate, lactose, calcium or sodium phosphate; disintegrating agents, such as croscarmellose sodium, cross-linked povidone, maize starch, or alginic acid; binding agents, such as povidone, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time material such as glyceryl monostearate or glyceryl distearate alone or with a wax may be employed.

Formulations for oral use may be also presented as hard gelatin capsules where the active ingredient is mixed with an inert solid diluent, for example celluloes, lactose, calcium phosphate or kaolin, or as soft gelatin capsules wherein the active ingredient is mixed with non-aqueous or oil medium, such as glycerin, propylene glycol, polyethylene glycol, peanut oil, liquid paraffin or olive oil.

In another embodiment, pharmaceutical compositions of the invention may be formulated as suspensions comprising a compound of the present invention in admixture with at least one pharmaceutically acceptable excipient suitable for the manufacture of a suspension. In yet another embodiment, pharmaceutical compositions of the invention may be formulated as dispersible powders and granules suitable for preparation of a suspension by the addition of suitable excipients.

Excipients suitable for use in connection with suspensions include suspending agents, such as sodium carboxymethylcellulose, methylcellulose, hydroxypropyl methycelluse, sodium alginate, polyvinylpyrrolidone, gum tragacanth, gum acadia, dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycethanol), a condensation product of ethylene oxide with a partial ester derived from a fatty acid and a hexitol anhydride (e.g., polyoxyethylene sorbitan monooleate), and thickening agents, such as carbomer, beeswax, hard paraffin or cetyl alcohol. The suspensions may also contain one or more preservatives such as acetic acid, methyl and/or n-propyl p-hydroxy-benzoate; one or more coloring agents; one or more flavoring agents; and one or more sweetening agents such as sucrose or saccharin.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth; naturally occurring phosphatides, such as soybean lecithin, esters or partial esters derived from fatty acids; hexitol anhydrides, such as sorbitan monooleate; and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

Additionally, the pharmaceutical compositions of the invention may be in the form of a sterile injectable preparation, such as a sterile injectable aqueous emulsion or oleaginous suspension. This emulsion or suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,2-propane-diol. The sterile injectable preparation may also be prepared as a lyophilized powder. Among the acceptable vehicles and solvents that may be employed are water, Ringer's solution, and isotonic sodium choloride solution. In addition, sterile fixed oils may be employed as a solvent or suspending medium. For this purpose any bland fixed oil may be employed including synthetic mono- or diglycerides. In addition, fatty acids such as oleic acid may likewise be used in the preparation of injectables.

In one embodiment, the compounds of the present invention may be formulated for oral administration in a lipid-based formulation suitable for low solubility compounds. Lipid-based formulations can generally enhance the oral bioavailability of such compounds. As such, a preferred pharmaceutical composition of the invention comprises a therapeutically or prophylactically effective amount of a compound of the present invention, together with at least one pharmaceutically acceptable excipient selected from the group consisting of: medium chain fatty acids or propylene glycol esters thereof (e.g., propylene glycol esters of edible fatty acids such as caprylic and capric fatty acids) and pharmaceutically acceptable surfactants such as polyoxyl 40 hydrogenated castor oil.

In an alternative preferred embodiment, cyclodextrins may be added as aqueous solubility enhancers. Preferred cyclodextrins include hydroxypropyl, hydroxyethyl, glucosyl, maltosyl and maltotriosyl derivatives of $\alpha$, $\beta$-, and $\gamma$-cyclodextrin. A particularly preferred cyclodextrin solubility enhancer is hydroxypropyl-$\beta$-cyclodextrin (HPBC), which may be added to any of the above-described compositions to further improve the aqueous solubility characteristics of the compounds of the present invention. In one embodiment, the composition comprises 0.1% to 20% hydroxypropyl-$\beta$-cyclodextrin, more preferably 1% to 15% hydroxypropyl-$\beta$-cyclodextrin, and even more preferably from 2.5% to 10% hydroxypropyl-$\beta$-cyclodextrin. The amount of solubility enhancer employed will depend on the amount of the compound of the present invention in the composition.

Combination Therapy

It is also possible to combine any compound of the present invention with one or more other active ingredients useful in the treatment of tuberculosis, including compounds, in a unitary dosage form, or in separate dosage forms intended for simultaneous or sequential administration to a patient in need of treatment. When administered sequentially, the combination may be administered in two or more administrations. In an alternative embodiment, it is possible to administer one or more compounds of the present invention and one or more additional active ingredients by different routes.

The skilled artisan will recognize that a variety of active ingredients may be administered in combination with the compounds of the present invention that may act to augment or synergistically enhance the anti-tuberculosis activity of the compounds of the invention.

According to the methods of the invention, the combination of active ingredients may be: (1) co-formulated and administered or delivered simultaneously in a combined formulation; (2) delivered by alternation or in parallel as separate formulations; or (3) by any other combination therapy regimen known in the art. When delivered in alternation therapy, the methods of the invention may comprise administering or delivering the active ingredients sequentially, e.g., in separate solution, emulsion, suspension, tablets, pills or capsules, or by different injections in separate syringes. In general, during alternation therapy, an effective dosage of each active ingredient is administered sequentially, i.e., serially, whereas in simultaneous therapy, effective dosages of two or more active ingredients are administered together. Various sequences of intermittent combination therapy may also be used.

General Synthetic Methods

The compounds of the invention may be produced via methods known in the art. The following scheme is intended to present a typical synthetic approach for the preparation of the compounds of the invention. Scheme 1 illustrates a synthetic approach for acylating the C-13 alcohol with a carboxylic acid corresponding to the desired $R^1$ substituent. The starting material is reacted with the carboxylic acid in the presence of a nitrogen base such as dimethylaminopyridine (DMAP), providing the inventive compound in good yield.

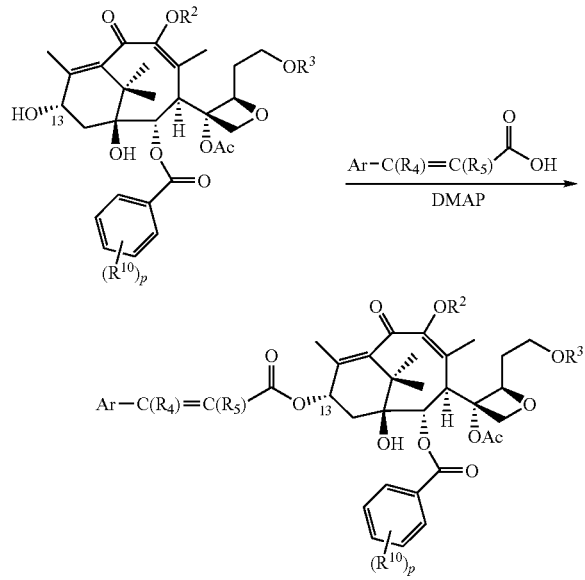

Scheme 1

EXPERIMENTAL

General Methods: $^1$H and $^{13}$C NMR spectra were measured on a Bruker AC-250 NMR spectrometer or a Varian 300, 400, or 500 NMR spectrometer. Melting points were measured on a Thomas Hoover Capillary melting point apparatus and are uncorrected. Optical rotations were measured on a Perkin-Elmer Model 241 polarimeter. TLC was performed on Merck DC-alufolien with Kieselgel 60F-254 and column chromatography was carried out on silica ge 60 (Merck: 230-400 mesh ASTM). High-resolution mass spectra were obtained from the University of California, Riverside Mass Spectrometry Facility, Riverside, Calif.; or Mass Spectrometry Laboratory, University of Illinois at Urbana-Champaign, Urban, Ill. Purity was determined with Shimadzu HPLC (LC2010A) system. HPLC1: Phenomenex®, Jupiter, C18, 10μ, 250×4.6 mm column; 70:30 v/v CH$_3$CN:H$_2$O over 10 min, followed by 70:30-90:10 v/v CH$_3$CN:H$_2$O over 3 min, then hold at 90/10 v/v CH$_3$CN:H$_2$O over 10 min; flow rate 1.0 mL/min; wavelength 254 nm. HPLC2: Waters, Nova-Pak®, C18, 3.9×150 mm column; 60:40 v/v CH$_3$CN:H$_2$O over 10 min, followed by 60:40-90:10 v/v CH$_3$CN:H$_2$O over 3 min, then hold at 90/10 v/v CH$_3$CN:H$_2$O over 10 min; flow rate 1.0 mL/min; wavelength 254 nm. HPLC3: Phenomenex®, Curosil-B, 5μ, 250×4.60 mm column, gradient 50:50-90:10 v/v CH$_3$CN:H$_2$O over 15 min, then hold at 90/10 v/v CH$_3$CN:H$_2$O for 10 min; flow rate 1.0 mL/min; wavelength 220 nm. HPLC4: Phenomenex®, Curosil-B, 5μ, 250×4.60 mm column, gradient 20:80-90:10 v/v CH$_3$CN:H$_2$O over 30 min, then hold at 90:10 v/v CH$_3$CN:H$_2$O for 5 min; flow rate 1.0 mL/min; wavelength 254 nm. HPLC5: Agilent, Zorbax, Eclipse XDB, C8, 5μ, 4.6×150 mm column; 50:50 v/v CH$_3$CN:H$_2$O over 10 min, followed by 50:50-90:10 v/v CH$_3$CN:H$_2$O over 5 min, then hold at 90/10 v/v CH$_3$CN:H$_2$O over 10 min; flow rate 0.5 mL/min; wavelength 254 nm.

Materials: The chemicals were purchased from Aldrich Co. and Sigma and purified before use by standard methods. Tetrahydrofuran was freshly distilled from sodium metal and benzophenone. Dichloromethane was also distilled immediately prior to use under nitrogen from calcium hydride. 10-Deacetylbaccatin III (DAB) and 14-□-hydroxy-10-deacetylbaccatin (14-OH-DAB) were obtained from Indena, SpA, Italy.

Acylation at the C-13 Position

To a solution of 7,9-Bis (triethylsilyl)-10-dehydro-7,8-seco-10-deacetylbaccatin III (0.15-0.2 M), DMAP (0.2 equiv) and the corresponding acid (2.2 equiv) in toluene/dichloromethan (1.1) was added DIC (4.0 equiv) at room temperature with stirring. After stirring for 10-15 h, the solvent was evaporated in vacuo. Purification of the crude product by short silica gel chromatography using ethyl acetate/hexane (4:1) as eluent afforded TES protected C-13 coupling product contaminated by DIC-acid complex, which were directly used in the next step.

To a solution of TES protected C-13 coupling product in a (1:1) mixture of pyridine and acetonitrile (4 mL/100 mg of starting material) at 0° C. was added a 70% solution of HF in pyridine (1 mL/100 mg of starting material) with stirring. After stirring overnight at room temperature, the reaction was quenched with NaHFCO$_3$ solution and extracted with ethyl acetate. The combined organic layers were washed with a saturated solution of copper sulfate and with water, then dried over magnesium sulfate, filtered and concentrated. Purification of the crude product by silica gel chromatography (hexanes/EtOAc=1/1) affords the inventive compound as a white solid.

The following compounds were synthesized by adapting this method.

13-[3-(2Naphthyl)prop-2-enoyl]-10-dehydro-7,8-seco-10-deacetylbaccatin III

Yield: 70%; mp: 157-160° C.; $[\alpha]_D^{20}$-178.4 (c 3.48, CHCl$_3$); $^1$H NMR (400 MHz, CDCl$_3$) δ 8.00-7.60 (m, 13H), 6.70 (bs, 1H), 6.12 (m, 1H, H-13), 5.64 (d, 1H, J=9 Hz), 5.40 (bs, 2H), 4.40 (bs, 2H), 3.90 (bs, 2H), 2.90-1.80 (m, 15H), 1.27 (s, 3H) 1.15 (s, 3H); $^{13}$C NMR (100 MHz, CDCl$_3$) δ 191.5 (10-C), 169.4 (4-Ac), 167.4 (1'-C), 166.5 (2-benz.), 149.0 (9-C), 146.8 (3'-C), 142.5 (11-C), 136.8 (12-C), 134.7 (arom), 134.0 (arom), 133.5 (arom), 131.7 (arom), 130.0 (arom), 129.8 (arom), 129.6 (arom), 129.1 (arom), 128.7 (arom), 128.0 (arom), 127.7 (arom), 127.4 (arom), 127.0 (arom), 124.4 (8-C), 123.4 (arom), 117.2 (2'-CH), 88.2 (5-CH), 86.4 (4-C), 80.3 (1-C), 75.1 (20-CH$_2$), 74.9 (2-CH), 69.3 (13-CH), 60.0 (7-CH$_2$), 48.7 (3-CH), 43.0 (15-C), 37.2 (6-CH$_2$), 29.9 (14-CH$_2$), 25.3 (16-CH$_3$), 21.3 (4-Ac), 20.9 (17-CH$_3$), 15.1 (18-CH$_3$), 14.6 (19-CH$_3$), HRMS (FAB) m/z calcd for C$_{42}$H$_{44}$O$_{11}$H$^+$: 725.2962, Found: 725.2958 (Δ=−0.4 ppm). HPLC1: 5.03 min, purity>98%; HPLC3: 8.11 min, purity>98%.

13-[3-(6Methoxy-2-naphthyl)prop-2-enoyl]-10-dehydro-7,8-seco-10-deacetylbaccatin III Yield: 64%; 1H NMR (400 MHz, CDCl$_3$) δ 8.00-7.40 (m, 10H), 7.18 (m, 2H), 6.65 (bs, 1H), 6.50 (s, 1H), 6.12 (m, 1H, H-13), 5.64 (d, 1H, J=9 Hz), 5.40 (bs, 2H), 4.40 (bs, 2H), 3.90 (bs, 5H), 2.90-1.40 (m, 15H), 1.27 (s, 3H), 1.15 (s, 3H).

HRMS (FAB) m/z calcd for $C_{43}H_{46}O_{12}H^+$: 755.3069, Found: 755.3061 ($\Delta=-0.7$ ppm). HPLC2: min, purity>95%; HPLC5: 6.70 min, purity>95%.

13-[(4-Phenylthiophenyl)-10-dehydro-7,8-seco-10-deacetylbaccatin III

Yield 68%; mp: 139-140° C.; $^1$H NMR (400 MHz, CDCl$_3$) $\delta$ 8.00 (bs, 2H), 7.75 (d, 1H, J=16 Hz), 7.60 (m, 1H), 7.45 (m, 5H), 7.37 (m, 3H), 7.22 (m, 3H), 6.50 (bs, 2H), 6.13 (m, 1H, 13-H), 5.63 (d, 1H, J=8 Hz), 5.30 (bs, 2H), 4.40 (bs, 2H), 3.80 (bs, 2H), 2.90-1.80 (m, 15H), 1.27 (s, 3H) 1.15 (s, 3H); $^{13}$C NMR (100 MHz, CDCl$_3$) $\delta$ 191.2 (10-C), 169.1 (1'-C), 167.2 (4-Ac), 166.2 (2-benz), 149.0 (9-C), 145.7 (3'-C), 142.2 (11-C), 141.3 (12-C), 133.8 (arom), 133.2 (arom), 133.0 (arom), 131.7 (arom), 129.5 (arom), 129.3 (arom), 129.0 (arom), 128.8 (arom), 128.7 (arom), 128.3 (arom), 124.1 (8-C), 116.4 (2'-C), 88.1 (5-CH), 86.1 (5-CH), 86.1 (4-C), 80.2 (1-C), 75.0 (20-CH$_2$), 74.6 (2-CH), 68.9 (13-CH), 59.9 (7-CH), 44.4 (3-CH), 42.7 (15-C), 36.9 (6-CH$_2$), 29.7 (14-CH$_2$), 25.1 (16-CH$_3$), 22.1 (4-Ac), 20.7 (17-CH$_3$), 14.8(18-CH$_3$), 14.4 (19-CH$_3$), HRMS (FAB) m/z calcd for $C_{44}H_{46}O_{11}SH^+$: 725.2839, Found: 783.2830 ($\Delta=-0.9$ ppm). HPLC1: 5.03 min, purity>97%; HPLC3: 10.14 min, purity>97%.

13-[4-Phenoxycinnamonyl]-10-dehydro-7,8-seco-10-deacetylbaccatin III

Yield: 60%; mp: 135-137° C.; 1H NMR (400 MHz, CDCl$_3$) $\delta$ (bs, 2H), 7.75, (d, J=16 Hz), 7.60-7.30 (m, 2H), 7.00 (m, 3H), 6.50 (bs, 2H), 6.13 (m, 1H, H-13), 5.63 (d, 1H, J=8 Hz), 5.30 (bs, 2H), 4.40 (bs, 2H) 3.80 (bs, 2H), 2.90-180 (m, 15H), 1.27 (s, 3H) 1.15 (s, 3H). HRMS (FAB) m/z calcd for $C_{44}H_{46}O_{12}H^+$: 767.3068, Found: 767.3060 ($\Delta=-0.8$ ppm). HPLC2: min, purity>95%; HPLC4: 24.37 min, purity>95%.

Evaluation of Biological Activities

Bacterial Strain. H37$_{Rv}$, the drug sensitive laboratory strain of *Mycobacterium tuberculosis* (MTB) as well as IMCJ946.K2, a multi-drug resistant MTB strain were used in this study. IMCJ 946.K2 is resistant to isoniazid (INH), rifampicin (RFP), ethambutol (EB), streptomycin (SM), kanamycin (KM), ethionamide (ETH), p-aminosalicylic acid (PAS), cycloserine (CS) and enviomycin (EVM).

Growth of Bacteria. The MTB strains were grown in MycoBroth (Kyokuto pharmaceutical Co., Ltd, Tokyo, Japan). When cultures reached an optical density of 0.4 to 0.5 at 530 nm (Vi-spec, Kyokuto pharmaceutical Co., Ltd), 100 µL of bacterial suspension was transferred to a tube containing fresh MycoBroth and grown until an optical density of 0.4 to 0.5 was reached.

Antibacterial Activity. The minimum inhibitory concentration (MIC$_{99}$) was determined by the Microplate Alamar Blue assay[2] with some modifications. Stock solutions of the compounds were prepared in DMSO at a concentration of 10 mM, and diluted into the culture broth to give the final desired concentration before every experiment. The optical density of the cultures in MycoBroth was adjusted to 0.16-0.2 at 530 nm (equal to that of a no. 1 McFarland standard) with Myco-Broth, and further diluted 1:50 in Middlebrook 7H9 broth (Difco, Becton Dickinson and Company, Sparks, Md.) supplemented with 10% of BBL™ Middlebrook OADC Enrichment (Becton Dickinson and Company) and 0.2% glycerol (7H9 broth). One hundred microliters of 7H9 broth was dispensed in each well of sterile 96-well flat bottom-plates (Nalge Nune International, Naperville, Ill.), and serial twofold dilutions of each compound were prepared directly in the plate. One hundred microliters of inoculum was added to each well, yielding a final volume of 200 µL per well. The wells filled with 7H9 broth served as drug-free (inoculum-only) controls. One hundred microliters of 7H9 broth was added to all outer-perimeter wells of 96-well plates to minimize evaporation of the medium in the test wells during incubation. The plates were sealed with Parafilm and were incubated with 5% $CO_2$ at 37° C. for 6 days. After 7 days of incubation, 50 µL of freshly prepared 1:1 mixture of 10× Alamar Blue (Trek Diagnostic Systems, Inc., Westlake, Ohio) reagent and 7H9 broth containing 10% Tween 80 (Sigma Chemical Co., St. Louis, Mo.) was added to each well, and the plates were further incubated overnight. A change in color from blue to pink indicated the growth of bacteria. The MIC$_{99}$ was defined as the lowest drug concentration of compound that prevented this change in color.

Cytotoxicity Assay. The human breast cancer-derived cell line MCF7 was provided by K. Yasuda, Dokkyo University, Tochigi, Japan, while the human lung cancer cell line A549 was purchased from Riken BioResource Center, Tsukuba, Japan. Cells were plated at $5 \times 10^4$/well in 96-well plates, and cultured for 3 days in the presence of serial diluted compounds. At the end of this time, the number of viable cells was determined by a quantitative colorimetric staining assay using a tetrazolium sale (MTT, Sigma Chemical Co.)[3] The inhibitory concentration (IC$_{50}$) of each compound was determined as the concentration required to inhibit 50% of the growth of the MCF7 and A549 cells.

REFERENCES (1) Ojima et al., Design, Synthesis and SAR of Novel Taxane-Based Multi-Drug Resistance Reversal Agents. *J. Med. Chem.* 2005, 48, 2218-2228

(2) Franzblau et al., Rapid, low-technology MIC determination with clinical *Mycobacterium tuberculosis* isolates by using the microplate Alamar Blue assay. *J. Clin Microbiol.* 1998, 36, 362-366.

(3) Kirikae et al., Structural significance of the benzoyl group at the C-3'-N position of paclitaxel for nitric oxide and tumor necrosis factor production by murine macrophages. *Biochem Biophys Res Commun.* 1998, 246, 698-704.

Scanning Electron Microscopy

SEM Ultrastructual analysis of *M. tuberculosis* treated with FtsZ inhibitors. Treated bacteria were fixed with 2.5% glutaraldehyde in buffer consisting of 0.1 M sodium cacodylate, 5 mM $CaCl_2$ and 5 mM $MgCl_2$ (pH 7.2). Complete fixation was accomplished incubation for 1 hr at room temperature followed by repeated washing with 0.1 M sodium cacodylate buffer followed by overnight fixation at 4C. Cells were post-fixed processed by ruinsin in 0.1M Sodium cacodylate buffer followed by 1 hr treatment with 1% $OsO_4$ in the same buffer. The bacteria were then pelleted and subsequently dehydrated in a graded series of acetone (25-100%). The cells were then examined with JOEL JEM-100CX electron microscope (JOEL Ltd. Japan). Significant reductions in the number of Bacteria were seen.

What is claimed is:

1. A chemical compound having the formula (I):

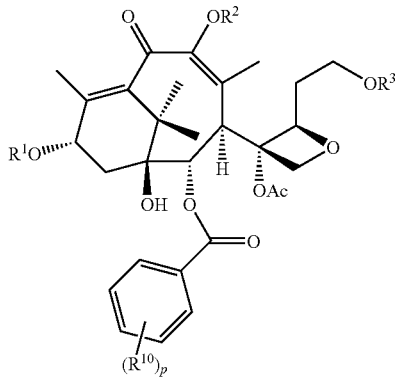

wherein

R$^1$ represents:

Ar—C(R$^4$)=C(R$^5$)—CO—

Ar is a carbocyclic aromatic ring or fused ring system haveing 6 to 20 carbon atoms, wherein the carbocyclic aromatic ring or fused ring system is unsubstituted, or is substituted at any position with one or more substituents selected from the group consisting of R$^6$, R$^7$, R$^8$, and Ar$^1$;

R$^2$ and R$^3$ are the same or different and each is selected from the group consisting of R$^9$, C(O)R$^9$, C(O)OR$^9$, C(O)OAr$^1$, C(O)Ar$^1$, C(O)N(Ar$^1$)$_2$, C(O)NR$^9$Ar$^1$, C(O)N(R$^9$)$_2$, and C(O)(CH$_2$)$_n$N(R$^9$)$_2$;

R$^4$ and R$^5$ are the same or different and each is selected from the group consisting of R$^9$, Ar$^1$, OAr$^1$, halo, OR$^9$, SR$^9$, N(R$^9$)$_2$, OC(O)R$^9$, R$^9$NC(O)R$^9$, OC(O)N(R$^9$)$_2$, R$^9$NC(O)OR$^9$, N(Ar$^1$)$_2$, NR$^9$Ar$^1$, R$^9$NC(O)Ar$^1$, OC(O)N(Ar$^1$)$_2$, R$^9$NC(O)OAr$^1$, Ar$^1$NC(O)R$^9$, Ar$^1$NC(O)OR$^9$, Ar$^1$NC(O)Ar$^1$, and Ar$^1$NC(O)OAr$^1$;

R$^6$ in each occurrence may be the same or different, and represents an alkyl group having 1-6 carbon atoms;

R$^7$ in each occurrence may be the same or different and is selected from the group consisting of halo, nitro, (R$^9$)$_2$N, R$^9$—S, R$^9$—O, (Ar$^2$)$_2$N, Ar$^2$—NR$^9$, Ar$^2$—S, and Ar$^2$—O;

R$^8$ in each occurrence may be the same or different, and is selected from the group consisting of X—R$^9$ and X—Ar$^2$, wherein X is selected from the group consisting of C(O)—, OC(O)—, C(O)O—, OC(O)O—, R$^9$NC(O)—, C(O)NR$^9$—, OC(O)NR$^9$, R$^9$NC(O)O—,; Ar$^2$NC(O)—, C(O)NAr$^2$—, OC(O)NAr$^2$ and Ar$^2$NC(O)O—;

R$^9$ in each occurrence may be the same or different and is selected from the group consisting of hydrogen and an alkyl group having 1-20 carbon atoms, wherein the alkyl group may be unsubstituted or substituted at any position with one or more substituents of R$^{11}$;

R$^{10}$ in each occurrence may be the same or different and is selected from the group consisting of halo, nitro, R$^6$, R$^6$—O, HO, (R$^6$)$_2$N, R$^6$NH, NH$_2$, R$^6$S, HS, CN, and N$_3$;

R$^{11}$ in each occurrence may be the same or different and is selected from the group consisting of R$^6$, CN, N$_3$, (R$^6$)$_2$N, HNR$^6$, NH$_2$, R$^6$—S, HS, R$^6$—O, HO, (Ar$^2$)$_2$N, Ar$^2$—NR$^6$, Ar$^2$—NH, Ar$^2$—S, and Ar$^2$—O;

Ar$^1$ in each occurrence may be the same or different, and is a carbocyclic aromatic ring or fused ring system having 6 to 20 carbon atoms, wherein the carbocyclic aromatic ring or fused ring system is unsubstituted or is sustituted at any position with one or more substituent selected from the group consisting of R$^6$, R$^7$, R$^8$, and Ar$^2$;

Ar$^2$ in each occurrence may be the same or different, and is a carbocyclic aromatic ring or fused ring system having 6 to 20 carbon atoms, wherein the carbocyclic aromatic ring or fused ring system is unsubstituted or is substituted at any position with one or more substituents of R$^{10}$;

n is 1 to 3; and p is 0 to 5, with the provision that R$^{10}$ in each occurrence may be the same or different when p is greater than 1.

2. The compound of claim 1, wherein

Ar is a carbocyclic aromatic ring or fused ring system haveing 6 to 10 carbon atoms, wherein the carbocyclic aromatic ring or fused ring system is unsubstituted or is substituted at any position with one or more substituents selected from the group consisting of R$^6$, R$^7$, R$^8$, and Ar$^1$;

Ar$^1$ is a carbocyclic aromatic ring or fused ring system having 6 to 10 carbon atoms, wherein the carbocyclic aromatic ring or fused ring system is unsubstituted or is substituted at any position with one or more substituents selected from the group consisting of R$^6$, R$^7$, R$^8$, and Ar$^2$;

Ar$^2$ is a carbocyclic aromatic ring or fused ring system having 6 to 10 carbon atoms, wherein the carbocyclic aromatic ring or fused ring system is unsubstituted or is substituted at any position with one or more substituents of R$^{10}$;

R$^6$ is an alkyl group having 1 to 4 carbon atoms;

R$^7$ is selected from the group consisting of halo, (R$^9$)$_2$N, R$^9$—O, (Ar$^2$)$_2$N, Ar$^2$—NR$^9$, and Ar$^2$—O;

R$^8$ is selected from the group consisting of X—R$^9$ and X—Ar$^2$, wherein X is selected from the group consisting of C(O)—, OC(O)—, C(O)O—, R$^9$NC(O)—, C(O)NR$^9$—, Ar$^2$NC(O)—, and C(O)NAr$^2$—;

R$^9$ is selected from the group consisting of H and an alkyl group having 1 to 4 carbon atoms, wherein the alkyl group may be unsubstituted or substituted at any position with one or more substituents of R$^{11}$;

R$^{10}$ is selected from the group consisting of halo, R$^6$, R$^6$—O, HO, (R$^6$)$_2$N, R$^6$NH, and NH$_2$; and R$^{11}$ is selected from the group consisting of halo, (R$^6$)$_2$N, HNR$^6$, NH$^2$, R$^6$—O, HO, (Ar$^2$)$_2$N, Ar$^2$—NR$^6$, Ar$^2$—NH, and Ar$^2$—O.

3. The compound of claim 1, wherein

Ar$^1$ is a carbocyclic aromatic ring or fused ring system having 6 to 10 carbon atoms, wherein the carbocyclic aromatic ring or fused ring system is unsubstituted or is substituted at any position with one or more substituents selected from the group consisting of R$^6$, R$^7$, R$^8$, and Ar$^2$;

Ar$^2$ is a carbocyclic aromatic ring or fused ring system having 6 to 10 carbon atoms, wherein the carbocyclic aromatic ring or fused ring system is unsubstituted or is substituted at any position with one or more substituents of R$^{10}$;

R$^6$ is an alkyl group having 1 to 4 carbon atoms;

R$^7$ is selected from the group consisting of halo, (R$^9$)$_2$N, R$^9$—O, (Ar$^2$)$_2$N, Ar$^2$—NR$^9$, and Ar$^2$—O;

R$^8$ is selected from the group consisting of X—R$^9$ and X—Ar$^2$, wherein X is selected from the group consisting of C(O)—, OC(O)—, C(O)O—, R$^9$NC(O)—, C(O)NR$^9$—, Ar$^2$NC(O)—, and C(O)NAr$^2$—;

R$^9$ is selected from the group consisting of H and an alkyl group having 1 to 4 carbon atoms, wherein the alkyl group may be unsubstituted or substituted at any position with one or more substituents of $R^{11}$; and $R^{10}$ is selected from the group consisting of halo, $R^6$, $R^6$—O, HO, $(R^6)_2$N, $R^6$NH, and $NH_2$; and $R^{11}$ is selected from the group consisting of halo, $(R^6)_2$N, $HNR^6$, $NH^2$, $R^6$—O, HO, $(Ar^2)_2$N, $Ar^2$—$NR^6$, $Ar^2$—NH, and $Ar^2$—O.

4. The compound of claim 1, wherein $Ar^2$ is a carbocyclic aromatic ring or fused ring system having 6 to 10 carbon atoms, wherein the carbocyclic aromatic ring or fused ring system is unsubstituted or is substituted at any position with one or more substituents of $R^{10}$;

$R^6$ is an alkyl group having 1 to 4 carbon atoms; and $R^{10}$ is selected from the group consisting of halo, $R^6$, $R^6$—O, HO, $(R^6)_2$N, $R^6$NH, and $NH_2$.

5. The compound of claim 1, wherein $R^2$ and $R^3$ are each selected from the group consisting of H, $C(O)R^9$, $C(O)Ar^1$, and $C(O)(CH_2)_nN(R^9)_2$;

$Ar^1$ is a carbocyclic aromatic ring or fused ring system having 6 to 10 carbon atoms, wherein the carbocyclic aromatic ring or fused ring system is unsubstituted or is substituted at any position with one or more substituents selected from the group consisting of $R^6$, $R^7$, $R^8$, and $Ar^2$;

$Ar^2$ is a carbocyclic aromatic ring or fused ring system having 6 to 10 carbon atoms, wherein the carbocyclic aromatic ring or fused ring system is unsubstituted or is substituted at any position with one or more substituents of $R^{10}$;

$R^6$ is an alkyl group having 1 to 4 carbon atoms;

$R^7$ is selected from the group consisting of halo, $(R^9)_2$N, $R^9$—O, $(Ar^2)_2$N, $Ar^2$—$NR^9$, and $Ar^2$—O;

$R^8$ is selected from the group consisting of X—$R^9$ and X—$Ar^2$, wherein X is selected from the group consisting of C(O)—, OC(O)—, C(O)O—, $R^9$NC(O)—, C(O)$NR^9$—, $Ar^2$NC(O)—, and C(O)$NAr^2$—;

$R^9$ is selected from the group consisting of H and an alkyl group having 1 to 4 carbon atoms, wherein the alkyl group may be unsubstituted or substituted at any position with one or more substituents of $R^{11}$;

$R^{10}$ is selected from the group consisting of halo, $R^6$, $R^6$—O, HO, $(R^6)_2$N, $R^6$NH, and $NH_2$;

$R^{11}$ is selected from the group consisting of halo, $(R^6)_2$N, $HNR^6$, $NH^2$, $R^6$—O, HO, $(Ar^2)_2$N, $Ar^2$—$NR^6$, $Ar^2$—NH, and $Ar^2$—O; and n is 1 to 3.

6. The compound of claim 1, wherein $R^4$ and $R^5$ are each selected from the group consisting of $R^9$, $Ar^1$, $OAr^1$, halo, $OR^9$, $N(R^9)_2$, $OC(O)R^9$, $R^9NC(O)R^9$, $N(Ar^1)_2$, $NR^9Ar^1$, $R^9NC(O)Ar^1$, $Ar^1NC(O)R^9$, and $Ar^1NC(O)Ar^1$;

$Ar^1$ is a carbocyclic aromatic ring or fused ring system having 6 to 10 carbon atoms, wherein the carbocyclic aromatic ring or fused ring system is unsubstituted or substituted at any position with one or more substituents selected from the group consisting of $R^6$, $R^7$, $R^8$, and $Ar^2$;

$Ar^2$ is a carbocyclic aromatic ring or fused ring system having 6 to 10 carbon atoms, wherein the carbocyclic aromatic ring or fused ring system is unsubstituted or is substituted at any position with one or more substituents of $R^{10}$;

$R^6$ is an alkyl group having 1 to 4 carbon atoms;

$R^7$ is selected from the group consisting of halo, $(R^9)_2$N, $R^9$—O, $(Ar^2)_2$N, $Ar^2$—$NR^9$, and $Ar^2$—O;

$R^8$ is selected from the group consisting of X—$R^9$ and X—$Ar^2$, wherein X is selected from the group consisting of C(O)—, OC(O)—, C(O)O—, $R^9$NC(O)—, C(O)$NR^9$—, $Ar^2$NC(O)—, and C(O)$NAr^2$—;

$R^9$ is selected from the group consisting of H and an alkyl group having 1 to 4 carbon atoms, wherein the alkyl group may be unsubstituted or substituted at any position with one or more substituents of $R^{11}$;

$R^{10}$ is selected from the group consisting of halo, $R^6$, $R^6$—O, HO, $(R^6)_2$N, $R^6$NH, and $NH_2$; and $R^{11}$ is selected from the group consisting of halo, $(R^6)_2$N, $HNR^6$, $NH^2$, $R^6$—O, HO, $(Ar^2)_2$N, $Ar^2$—$NR^6$, $Ar^2$—NH, and $Ar^2$—O.

7. The compound of claim 1, wherein $R^6$ is an alkyl group having 1 to 4 carbon atoms.

8. The compound of claim 1, wherein $R^7$ is selected from the group consisting of halo, $(R^9)_2$N, $R^9$—O, $(Ar^2)_2$N, $Ar^2$—$NR^9$, and $Ar^2$—O;

$Ar^2$ is a carbocyclic aromatic ring or fused ring system having 6 to 10 carbon atoms, wherein the carbocyclic aromatic ring or fused ring system is unsubstituted or is substituted at any position with one or more substituents of $R^{10}$;

$R^6$ is an alkyl group having 1 to 4 carbon atoms;

$R^9$ is selected from the group consisting of H and an alkyl group having 1 to 4 carabon atoms, wherein the alkyl group may be unsubstituted or substituted at any position with one or more substituents of $R^{11}$;

$R^{10}$ is selected from the group consisting of halo, $R^6$, $R^6$—O, HO, $(R^6)_2$N, $R^6$NH, and $NH_2$; and $R^{11}$ is selected from the group consisting of halo, $(R^6)_2$N, $HNR^6$, $NH^2$, $R^6$—O, HO, $(Ar^2)_2$N, $Ar^2$—$NR^6$, $Ar^2$—NH, and $Ar^2$—O.

9. The compound of claim 1, wherein $R^8$ is selected from the group consisting of X—$R^9$ and X—$Ar^2$, wherein X is selected from the group consisting of C(O)—, OC(O)—, C(O)O—, $R^9$NC(O)—, C(O)$NR^9$—, $Ar^2$NC(O)—, and C(O)$NAr^2$—;

$Ar^2$ is a carbocyclic aromatic ring or fused ring system having 6 to 10 carbon atoms, wherein the carbocyclic aromatic ring or fused ring system or the is unsubstituted or is substituted at any position with one or more substituents of $R^{10}$;

$R^6$ is an alkyl group having 1 to 4 carbon atoms;

$R^9$ is selected from the group consisting of H and an alkyl group having 1 to 4 carabon atoms, wherein the alkyl group may be unsubstituted or substituted at any position with one or more substituents of $R^{11}$;

$R^{10}$ is selected from the group consisting of halo, $R^6$, $R^6$—O, HO, $(R^6)_2$N, $R^6$NH, and $NH_2$; and $R^{11}$ is selected from the group consisting of halo, $(R^6)_2$N, $HNR^6$, $NH^2$, $R^6$—O, HO, $(Ar^2)_2$N, $Ar^2$—$NR^6$, $Ar^2$—NH, and $Ar^2$—O.

10. The compound of claim 1, wherein $R^9$ is selected from the group consisting of H and an alkyl group having 1 to 4 carabon atoms, wherein the alkyl group may be unsubstituted or substituted at any position with one or more substituents of $R^{11}$;

$Ar^2$ is a carbocyclic aromatic ring or fused ring system having 6 to 10 carbon atoms, wherein the carbocyclic aromatic ring or fused ring system is unsubstituted or is substituted at any position with one or more substituents of $R^{10}$;

$R^6$ is an alkyl group having 1 to 4 carbon atoms;

$R^{10}$ is selected from the group consisting of halo, $R^6$, $R^6$—O, HO, $(R^6)_2$N, $R^6$NH, and $NH_2$; and $R^{11}$ is selected from the group consisting of halo, $(R^6)_2$—N, $HNR^6$, $NH_2$, $R^6$—O, HO, $(Ar^2)_2$—N, $Ar^2$—$NR^6$, $Ar^2$—NH, and $Ar^2$—O.

11. The compound of claim 1, wherein
$R^{10}$ is selected from the group consisting of halo, $R^6$, $R^6$—O, HO, $(R^6)_2N$, $R^6NH$, and $NH_2$; and
$R^6$ is an alkyl group having 1 to 4 carbon atoms.

12. The compound of claim 1, wherein
$R^{11}$ is selected from the group consisting of halo, $(R^6)_2$—N, $HNR^6$, $NH_2$, $R^6$—O, HO, $(Ar^2)_2$—N, $Ar^2$—$NR^6$, $Ar^2$—NH, and $Ar^2$—O.
$Ar^2$ is a carbocyclic aromatic ring or fused ring system having 6 to 10 carbon atoms, wherein the carbocyclic aromatic ring or fused ring system is unsubstituted or is substituted at any position with one or more substituents of $R^{10}$;
$R^6$ is an alkyl group having 1 to 4 carbon atoms; and
$R^{10}$ is selected from the group consisting of halo, $R^6$, $R^6$—O, HO, $(R^6)_2N$, $R^6NH$, and $NH_2$.

13. The compound of claim 1, wherein
Ar is a carbocyclic aromatic ring or fused ring system having 6 to 10 carbon atoms, wherein the carbocyclic aromatic ring or fused ring system or the is unsubstituted or is substituted at any position with one or more substituent selected from the group consisting of $R^6$, $R^7$, $R^8$, and $Ar^1$;
$Ar^1$ is a carbocyclic aromatic ring or fused ring system having 6 to 10 carbon atoms, wherein the carbocyclic aromatic ring or fused ring system is unsubstituted or is substituted at any position with one or more substituents selected from the group consisting of $R^6$, $R^7$, $R^8$, and $Ar^2$;
$Ar^2$ is a carbocyclic aromatic ring or fused ring system having 6 to 10 carbon atoms, wherein the carbocyclic aromatic ring or fused ring system is unsubstituted or is substituted at any position with one or more substituents of $R^{10}$;
$R^2$ and $R^3$ are selected from the group consisting of H, $C(O)R^9$, $C(O)OR^9$, $C(O)OAr^1$, and $C(O)Ar^1$, $C(O)N(Ar^1)_2$, $C(O)NR^9Ar^1$, $C(O)N(R^9)_2$, and $C(O)(CH_2)_nN(R^9)_2$;
$R^4$ and $R^5$ are each selected from the group consisting of $R^9$, $Ar^1$, $OAr^1$, halo, $OR^9$, $N(R^9)_2$, $OC(O)R^9$, $R^9NC(O)R^9$, $N(Ar^1)_2$, $NR^9Ar^1$, $R^9NC(O)Ar^1$, $Ar^1NC(O)R^9$, and $Ar^1NC(O)Ar^1$;
$R^6$ is an alkyl group having 1 to 4 carbon atoms;
$R^7$ is selected from the group consisting of halo, $(R^9)_2N$, $R^9$—O, $(Ar^2)_2N$, $Ar^2$—$NR^9$, and $Ar^2$—O;
$R^8$ is selected from the group consisting of X—$R^9$ and X—$Ar^2$, wherein X is selected from the group consisting of C(O)—, OC(O)—, C(O)O—, $R^9NC(O)$—, $C(O)NR^9$—, $Ar^2NC(O)$—, and $C(O)NAr^2$—;
$R^9$ is selected from the group consisting of H and an alkyl group having 1 to 4 carbon atoms, wherein the alkyl group may be unsubstituted or substituted at any position with one or more substituents of $R^{11}$;
$R^{10}$ is selected from the group consisting of halo, $R^6$, $R^6$—O, HO, $(R^6)_2N$, $R^6NH$, and $NH_2$;
$R^{11}$ is selected from the group consisting of halo, $(R^6)_2N$, $HNR^6$, $NH_2$, $R^6$—O, HO, $(Ar^2)_2N$, $Ar^2$—$NR^6$, $Ar^2$—NH, and $Ar^2$—O; and
n is 1 to 3.

14. The compound of claim 1, where Ar and $Ar^1$ may be the same or different, and each is a carbocyclic aromatic ring or fused ring system having 6 to 10 carbon atoms, wherein the carbocyclic aromatic ring or fused ring system is unsubstituted or substituted at any position with one or more substituents selected from the group consisting of halo, phenyl, methoxy, ethoxy, methyl, ethyl, $NH_2$, dimethylamino, and diethylamino.

15. The compound of claim 1, wherein:
$R^2$ and $R^3$ are each selected from the group consisting of H, $C(O)R^9$, $C(O)OR^9$, $C(O)OAr^1$, $C(O)Ar^1$, $C(O)(CH_2)_nN(R^9)_2$;
$Ar^1$ is a carbocyclic aromatic ring or fused ring system having 6 to 10 carbon atoms, wherein the carbocyclic aromatic ring or fused ring system is unsubstituted or is substituted at any position with one or more substituents selected from the group consisting of halo, phenoxy, phenyl, methoxy, ethoxy, methyl, ethyl, $NH_2$, dimethylamino, and diethylamino;
$R^9$ is selected from the group consisting of H and an alkyl group having 1 to 4 carbon atoms, wherein the alkyl group may be unsubstituted or substituted at any position with one or more substituents selected from the group consisting of halo, methoxy, ethoxy, $NH_2$, dimethylamino, and diethylamino; and
n is 1 to 3.

16. The compound of claim 1, wherein:
$R^4$ and $R^5$ are each selected from the group consisting of $R^9$, $Ar^1$, $OAr^1$, halo, $OR^9$, $N(R^9)_2$, $OC(O)R^9$, $R^9NC(O)R^9$, $N(Ar^1)_2$, $NR^9Ar^1$, $R^9NC(O)Ar^1$, $Ar^1NC(O)R^9$, and $Ar^1NC(O)Ar^1$;
$Ar^1$ is a carbocyclic aromatic ring or fused ring system having 6 to 10 carbon atoms, wherein the carbocyclic aromatic ring or fused ring system is unsubstituted or substituted at any position with one or more substituents selected from the group consisting of halo, phenyl, methoxy, ethoxy, methyl, ethyl, $NH_2$, dimethylamino, and diethylamino; and
$R^9$ is selected from the group consisting of H and an alkyl group having 1 to 4 carbon atoms, wherein the alkyl group may be unsubstituted or substituted at any position with one or more substituents selected from the group consisting of halo, methoxy, ethoxy, $NH_2$, dimethylamino, and diethylamino.

17. The compound of claim 1, wherein Ar and $Ar^1$ may be the same or different, and each is selected from the group consisting of phenyl and, naphthyl.

18. The compound of claim 1, wherein:
Ar and $Ar^1$ may be the same or different, and each is a carbocyclic aromatic ring or fused ring system having 6 to 10 carbon atoms, wherein the carbocyclic aromatic ring or fused ring system is unsubstituted or substituted at any position with one or more substituents selected from the group consisting of halo, phenyl, methoxy, ethoxy, methyl, ethyl, $NH_2$, dimethylamino, and diethylamino;
$R^2$ and $R^3$ are each selected from the group consisting of H, $C(O)R^9$, $C(O)OR^9$, $C(O)OAr^1$, and $C(O)Ar^1$, $C(O)(CH_2)_nN(R^9)_2$;
$R^4$ and $R^5$ are each selected from the group consisting of $R^9$, $Ar^1$, $OAr^1$, halo, $OR^9$, $N(R^9)_2$, $OC(O)R^9$, $R^9NC(O)R^9$, $N(Ar^1)_2$, $NR^9Ar^1$, $R^9NC(O)Ar^1$, $Ar^1NC(O)R^9$, and $Ar^1NC(O)Ar^1$;
$R^9$ is selected from the group consisting of H and an alkyl group having 1 to 4 carbon atoms, wherein the alkyl group may be unsubstituted or substituted at any position with one or more substituents selected from the group consisting of halo, methoxy, ethoxy, $NH_2$, dimethylamino, and diethylamino; and n is 1 to 3.

19. A chemical compound having the formula (II):

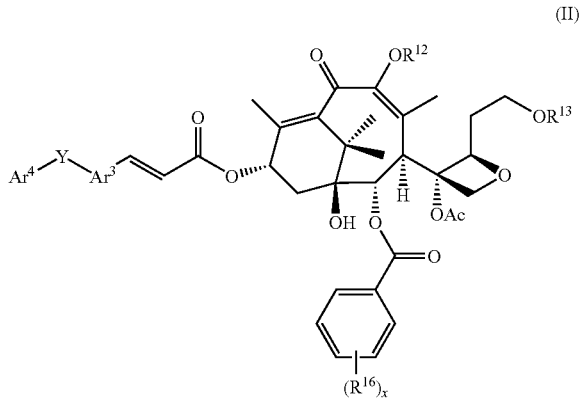

(II)

wherein
Ar$^3$ is a divalent carbocyclic aromatic ring or fused ring system having 6 to 10 carbon atoms, wherein the carbocyclic aromatic ring or fused ring system is unsubstituted or substituted at any position with one or more substituents selected from the group consisting of halo, phenoxy, phenyl, methoxy, ethoxy, methyl, ethyl, NH$_2$, dimethylamino, and diethylamino;

Ar$^4$ is a carbocyclic aromatic ring or fused ring system having 6 to 10 carbon atoms, wherein the carbocyclic aromatic ring or fused ring system is unsubstituted or is substituted at any position with one or more substituents selected from the group consisting of halo, phenoxy, phenyl, methoxy, ethoxy, methyl, ethyl,, NH$_2$, dimethylamino, and diethylamino;

Y is selected from the group consisting of O, S, NH, and NR$^{15}$;

R$^{12}$ and R$^{13}$ are the same or different and each is selected from the group consisting of H, R$^{15}$, C(O)R$^{15}$, C(O)OR$^{15}$C(O)OAr$^3$, C(O)Ar$^3$, and C(O)(CH$_2$)$_n$N(R$^{15}$)$_2$;

R$^{15}$ is an alkyl group having 1 to 4 carbon atoms;

R$^{16}$ in each occurrence may be the same or different, may occur at any position, and is selected from the group consisting of halo, nitro, R$^{15}$, R$^{15}$—O, HO, (R$^{15}$)$_2$N, R$^{15}$NH, NH$_2$, R$^{15}$S, HS, CN, and N$_3$;

k in 0 to 5, with the provision that R$^{16}$ in each occurrence may be the same or different when k is greater that 1; and n is 1 to 3.

20. The compound of claim 19, having the structure:

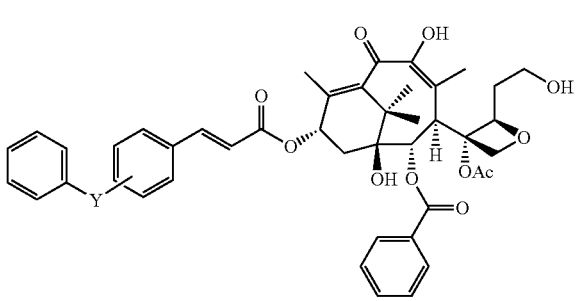

wherein Y is selected from the group consisting of O and S.

21. A chemical compound having the formula (III):

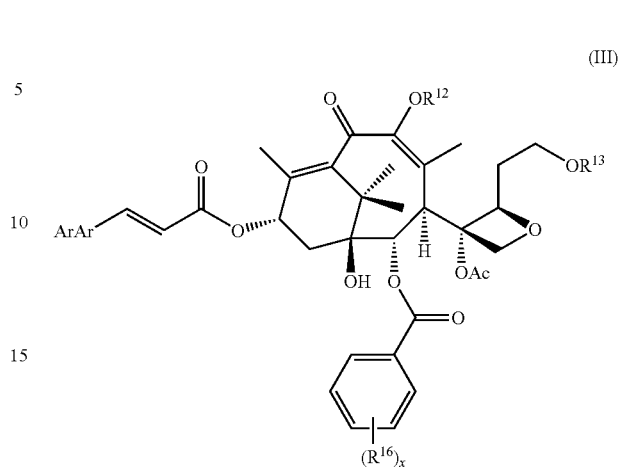

(III)

wherein
ArAr is a carbocyclic aromatic ring or fused ring system having 10 to 20 carbon atoms, wherein the carbocyclic aromatic fused ring system is unsubstituted or substituted with one or more substituents selected from the group consisting of halo, nitro, R$^{15}$, R$^{15}$—O, HO, (R$^{15}$)$_2$N, R$^{15}$NH, NH$_2$, R$^{15}$S, and HS;

R$^{12}$ and R$^{13}$ are the same or different and each is selected from the group consisting of H, R$^{15}$, C(O)R$^{15}$, C(O)OR$^{15}$C(O)OAr$^3$, C(O)Ar$^3$, and C(O)(CH$_2$)$_n$N(R$^{15}$)$_2$;

R$^{15}$ is an alkyl group having 1 to 4 carbon atoms; and

R$^{16}$ in each occurrence may be the same or different, may occur at any position, and is selected from the group consisting of halo, nitro, R$^{15}$, R$^{15}$—O, HO, (R$^{15}$)$_2$N, R$^{15}$NH, NH$_2$, R$^{15}$S, HS, CN, and N$_3$;

k in each occurrence may be the same or different, and is 0 to 5, with the provision that R$^{16}$ in each occurrence may be the same or different when k is greater that 1; and n is 1 to 3.

22. The compound of claim 21, having the structure;

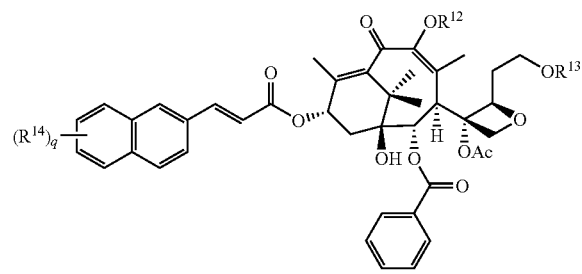

wherein
R$^{14}$ is selected from the group consisting of halo, nitro, R$^{15}$, R$^{15}$—O, HO, (R$^{15}$)$_2$N, R$^{15}$NH, and NH$_2$;

R$^{15}$ is an alkyl group having 1 to 4 carbon atoms; and q is 0 or 1.

* * * * *

UNITED STATES PATENT AND TRADEMARK OFFICE
CERTIFICATE OF CORRECTION

| | |
|---|---|
| PATENT NO. | : 7,615,653 B2 |
| APPLICATION NO. | : 11/684883 |
| DATED | : November 10, 2009 |
| INVENTOR(S) | : Ojima |

It is certified that error appears in the above-identified patent and that said Letters Patent is hereby corrected as shown below:

IN THE PATENT:

Column 3, line 66:

Now reads: "6 to 20"

Should read: --6 to 10--

Column 13, line 35:

Now reads: "of formula (I)"

Should read: --of formula (II)--

Column 25, line 62:

Now reads: "of $R^6$, CN"

Should read: --of halo, nitro, $R^6$, CN--

Signed and Sealed this

Thirteenth Day of April, 2010

David J. Kappos
*Director of the United States Patent and Trademark Office*